United States Patent [19]
Lardy et al.

[11] Patent Number: 5,932,765
[45] Date of Patent: Aug. 3, 1999

[54] NITROMETHYL KETONES, PROCESS FOR PREPARING THEM AND COMPOSITIONS CONTAINING THEM

[75] Inventors: Claude Lardy, Lyon; Jaques Barbanton, Brignais; Herve Dumas, Vaulx Milieu; Francois Collonges, Beynost; Phillippe Durbin, Villeurbanne, all of France

[73] Assignee: Merck Patent Gesellschaft Mit, Beschränkter Haftung, Germany

[21] Appl. No.: 08/955,624

[22] Filed: Oct. 22, 1997

[30] Foreign Application Priority Data

May 23, 1997 [EP] European Pat. Off. ............ 97108369

[51] Int. Cl.⁶ .................................................. C07C 233/00
[52] U.S. Cl. .......................... 564/163; 564/166; 564/169; 564/305; 568/308; 568/325; 568/329; 568/331
[58] Field of Search ..................................... 568/308, 325, 568/329, 331, 333; 564/123, 155, 163, 166, 169, 305, 124

[56] References Cited

U.S. PATENT DOCUMENTS

| | | |
|---|---|---|
| 3,983,156 | 9/1976 | Buckle et al. . |
| 3,984,565 | 10/1976 | Buckle et al. . |
| 4,117,137 | 9/1978 | Hardtmann . |
| 4,381,304 | 4/1983 | Palameta . |
| 4,382,088 | 5/1983 | Palameta . |
| 5,409,933 | 4/1995 | Kim et al. . |

OTHER PUBLICATIONS

CA:117:76465 abs of "Flavone C– glycoside for treatment of diseased associated with diabetes", Jp 04059788, Feb. 26, 1992.

Beilstein (BRN3320604) prep found in Aust J Chem by Johnstone 11, 62,562, 571, 1958.

CA:117:76464, abs of JP04059773, Jun. 1990.

CA95:6715 abs of Chem Pharm Bull by Hamada29(1) pp. 259–261, 1981.

CA:124202128 abs of Zh Obschch Khim by Gein, 65(8) pp. 1378–1380, 1995.

CA:109:128497 abs of Synthesis by Ashwell, (3) pp. 229–231, 1988.

CA:119:443324 abs of JP0543518, Feb. 1993.

*Primary Examiner*—Gary Geist
*Assistant Examiner*—Jean F Vollano
*Attorney, Agent, or Firm*—Millen, White, Zelano, & Branigan, P.C.

[57] ABSTRACT

The present invention relates to the compounds of formula:

(I)

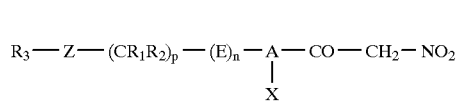

$$R_3-Z-(CR_1R_2)_p-(E)_n-\underset{X}{A}-CO-CH_2-NO_2$$

in which $R_1, R_2, R_3, E, A, X, Z, p$ and $n$ are as defined herein. These compounds are aldose reductase inhibitors.

10 Claims, No Drawings

NITROMETHYL KETONES, PROCESS FOR PREPARING THEM AND COMPOSITIONS CONTAINING THEM

The present invention relates to new nitromethyl ketones, to their preparation and to their use as medicaments, especially in the treatment or prevention of the complications of diabetes.

Diabetes is characterized by a high concentration of glucose in the blood. This glucose is normally metabolized by the enzyme hexokinase during the first stage of glycolysis, leading to the degradation into pyruvate. When the glucose concentration is too high, hexokinase becomes saturated and a second pathway for glucose metabolism comes into play. It is the polyol pathway which involves two enzymes successively: aldose reductase which converts glucose to sorbitol and sorbitol dehydrogenase which converts sorbitol to fructose. In the event of diabetes, the excess glucose accelerates the formation of sorbitol which tends to accumulate. This results in serious metabolic disturbances, such as for example an increase in osmotic pressure which can lead to tissue degeneration. Aldose reductase inhibitors are therefore useful for treating or preventing certain complications induced by diabetes.

Numerous products are described in the literature, such as aldose reductase inhibitors which are active in vitro and in vivo.

They are mainly derivatives of hydantoins, of succinimides and of acetic acids and more recently derivatives of sulfonylnitromethanes.

SUMMARY OF THE INVENTION

The present invention relates to nitromethyl ketone derivatives and their addition salts with physiologically acceptable bases, corresponding to the general formula (I):

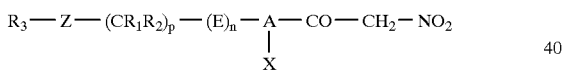

(I)

in which

A represents $C_6$–$C_{10}$ aryl or an optionally aromatic three- to ten-membered heterocycle in which one to four ring atoms are identical or different heteroatoms chosen from O, S and N;

X represents halogen, cyano, $C_1$–$C_7$ alkyl, trifluoromethyl, $C_2$–$C_7$ alkoxy or trifluoromethoxy;

$R_1$ and $R_2$, which are identical or different, represent a hydrogen atom, a $C_1$–$C_7$ alkyl group, a $C_3$–$C_{12}$ cycloalkyl group, a trifluoromethyl group, a $C_1$–$C_7$ alkoxy group or $R_1$ or $R_2$ together form an alkylene chain of the —$(CH_2)_r$— type, where r is chosen from 2, 3 and 4;

p is chosen from 0, 1, 2, 3, 4 and 5;

Z represents a bond, the divalent radical —CO—NH— in which the carbonyl function is linked to $R_3$, the divalent radical —$SO_2$—NH— in which the sulfonyl function is linked to $R_3$, a $C_2$–$C_7$ alkenylene radical, a sulfur atom, the sulfinyl group or a sulfonyl group;

$R_3$ represents a hydrogen atom; a halogen atom; a tri-($C_1$–$C_7$-alkyl)silyl group; a $C_1$–$C_7$ alkyl group optionally substituted with one or more identical or different Y radicals; a $C_6$–$C_{10}$ aryl group optionally substituted with one or more identical or different Y radicals; a $C_6$–$C_{10}$ aryloxy group optionally substituted with one or more identical or different Y radicals; a $C_3$–$C_{12}$ cycloalkyl group optionally substituted with one or more identical or different Y radicals; an optionally aromatic three- to ten-membered heterocycle in which one to four ring atoms are identical or different heteroatoms chosen from O, S and N, the heterocycle being optionally substituted with one or more identical or different Y radicals, or $R_3$ represents indanyl, 1,3-dihydro-1,3-dioxo-2H-isoindol-2-yl, 1,3-benzodioxolyl, 2-oxopiperidinyl or 2-[(4-nitromethylcarbonyl-3-chlorophenyl)aminocarbonyl]-1-(phenyl)ethyl;

Y represents a halogen atom, $C_1$–$C_7$ alkyl, $C_1$ $C_7$ alkoxy, trifluoromethyl, carboxy, carbamoyl, ($C_1$–$C_7$) alkylcarbamoyl, di-($C_1$–$C_7$) alkylcarbamoyl, $C_1$–$C_7$ alkoxycarbonyl, amino, $C_1$–$C_7$-alkylamino, di-($C_1$–$C_7$)-alkylamino, nitro, cyano, hydroxy, trifluoromethoxy, $C_3$–$C_{12}$ cycloalkyl, sulfo, $C_1$–$C_7$ alkylthio, $C_1$–$C_7$ alkylsulfinyl, $C_1$–$C_7$ alkylsulfonyl, $C_2$–$C_8$ alkylcarbonyl, $C_2$–$C_8$ alkylthiocarbonyl, $C_2$–$C_8$ alkylcarbonylamino, or $C_6$–$C_{10}$ aryl;

E represents a divalent radical chosen from:
(i) —CO—$NR_4$— in which the carbonyl group is linked to —$(CR_1R_2)_p$— and $R_4$ represents the radical —$(CH_2)_q$—$R_5$ where q is chosen from 0 and 1; and where $R_5$ represents a hydrogen atom; a $C_1$–$C_7$ alkyl group; a $C_6$–$C_{10}$ aryl group or an optionally aromatic three- to ten-membered heterocycle in which one to four ring atoms are identical or different heteroatoms chosen from O, N and S; or $R_5$ and $R_3$ together form a bond;
(ii) —$SO_2$—$NR_4$— in which the sulfonyl group is linked to —$(CR_1R_2)_p$— and $R_4$ is as defined above;
(iii) —$NR_4$— in which $R_4$ is as defined above;
(iv) —CH=N— in which the nitrogen atom is linked to A; and
(v) an oxygen atom;

n represents 0 or 1;

on the condition that —A(X)—$(E)_n$—$(CR_1R_2)_p$—Z—$R_3$ does not represent halophenyl, methylphenyl, dichlorophenyl, dimethylphenyl, 4-ethoxy-2-methylaminophenyl, methylindolyl, dimethylindolyl, 2-hydroxyphenyl substituted with a group X, 2-methoxyphenyl substituted with a group X and optionally substituted 2-fluorophenyl as defined above, and on the condition that when A represents pyridyl, X represents methyl and n is equal to 1, E does not represent —$NR_4$—.

These compounds are inhibitors of the enzyme aldose reductase and may be used in the treatment or prevention of the complications of diabetes: neurological, peripheral and autonomous complications, renal complications and ocular complications such as cataract and retinopathy.

The physiologically acceptable salts of the compounds of formula (I) comprise the salts formed with metals (such as sodium, potassium, calcium, magnesium, aluminum), or with bases such as ammonium hydroxide or substituted amines (such as diethylamine, triethylamine, piperidine, piperazine, morpholine) or basic amino acids (such as lysine, arginine) or with osamines (such as meglumine) or with amino alcohols (such as 3-aminobutanol, 2-aminoethanol).

The term "aryl" represents an aromatic mono- or bicyclic group comprising 6 to 10 carbon atoms, such as phenyl or naphthyl.

The term "heterocycle" denotes a mono- or bicyclic ring with an aromatic character or otherwise, comprising 3 to 10 ring atoms of which 1 to 4 are identical or different heteroatoms chosen from oxygen, sulfur and nitrogen, such as for example, the aziridinyl, oxiranyl, oxazolyl, furyl, tetrahydrofuranyl, thienyl, imidazolyl, pyridyl, pyrazinyl, benzothienyl, benzopyranyl, benzofuryl, benzothiazolyl, pyrimidinyl, pyridazinyl, piperidinyl, quinolyl, tetrahydroquinolyl, tetrazolyl, phthalazinyl, purinyl, indolyl, chromenyl, chromanyl, isochromanyl and pyrrolyl.

The term "cycloalkyl" denotes saturated hydrocarbon groups containing 3 to 12 carbon atoms, preferably 3 to 8, such as cyclopropyl, cyclobutyl, cyclopentyl, cyclohexyl, cycloheptyl, cyclooctyl, cyclononyl, cyclodecyl, cycloundecenyl and cyclododecyl.

The term "halogen" represents a fluorine, chlorine, bromine or iodine atom.

The term "alkyl" denotes a linear or branched hydrocarbon radical such as methyl, ethyl, propyl, isopropyl, butyl, tert-butyl, isobutyl, pentyl, hexyl, heptyl.

The term "alkoxy" denotes an alkyl group linked to an oxygen atom. Examples thereof are the methoxy, ethoxy, isopropyloxy, butoxy, hexyloxy radicals.

Likewise, "aryloxy" denotes an aryl radical as defined above linked to an oxygen atom, such as phenoxy and naphthyloxy.

According to the invention, "alkenylene" radical is understood to mean, moreover, a divalent hydrocarbon radical carrying one or more ethylenic double bonds such as, for example, —CH=CH—CH$_2$— or —CH=CH—CH=CH—.

"Carbamoyl" radical denotes the monovalent radical of formula —CO—NH$_2$. The radical "($C_1$-$C_7$) alkylcarbamoyl" denotes a carbamoyl radical substituted with a $C_1$-$C_7$ alkyl group on the nitrogen atom and the radical "di-($C_1$-$C_7$)alkylcarbamoyl" denotes a carbamoyl radical substituted on the nitrogen atom with two $C_1$-$C_7$ alkyl groups.

The radical "($C_1$-$C_7$)alkoxycarbonyl" denotes a radical R—C—CO— in which R represents a $C_1$-$C_7$ alkyl group.

The radical "($C_1$-$C_7$)alkylamino" denotes an amino group substituted on the nitrogen atom with a ($C_1$-$C_7$)alkyl radical and the radical "di-($C_1$-$C_7$)alkylamino" denotes an amino group substituted on the nitrogen atom with two ($C_1$-$C_7$) alkyl radicals.

The terms "alkylthio", "alkylsulfinyl" and "alkylsulfonyl" represent an alkyl group linked to a sulfur atom which is respectively nonoxidized, monooxidized or di-oxidized, such as methylthio, methylsulfinyl or methylsulfonyl.

Some compounds related to this type are known. For example, DE 2,415,350 describes antiallergic compounds of formula:

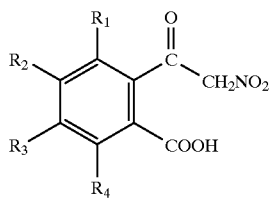

in which R$_1$, R$_2$, R$_3$, R$_4$, which are identical or different, may represent a hydrogen or halogen atom, an alkyl, alkoxy, aryl or arylalkyl group, a heterocycle or, two by two, a carbocycle or a heterocycle.

In patent DE 2,741,011, antihistaminic-antiallergic compounds are described, which are of the formula:

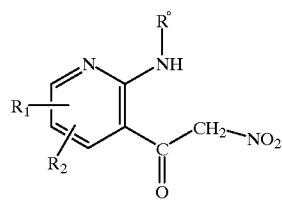

in which R° represents a hydrogen atom, a ($C_1$–$C_6$)alkyl, ($C_3$–$C_6$)cycloalkyl, ($C_3$–$C_6$)cycloalkyl-($C_1$–$C_2$)alkyl, ($C_3$–$C_6$)alkenyl or ($C_3$–$C_6$)alkynyl group or a radical of formula

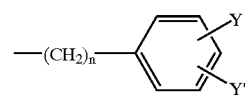

Nitromethyl ketone derivatives attached to polysubstituted naphthyridines and quinolones are described in patent EP 574 231 for an antibiotic activity.

Other nitromethyl ketone derivatives have been described in the literature, for example as synthesis intermediates, but the prior art does not refer at all to a potential therapeutic use of these compounds. There may be mentioned for example J. SETER, Israel J. Chem (1966) 4, 7–22 or BAKER D. C. and PUTT S. R., Synthesis (1978) 678–9 or FIELD G. F. and ZALLY W. J., Synthesis (1979) 295–6 or HAMADA Yasumasa et al., Chem. Pharm. Bull (1981) 29, 259–61.

The known nitromethyl ketone derivatives do not correspond to the formula (I) of the compounds of the invention; moreover, none of these compounds is described as having any inhibitory activity towards aldose reductase.

Preferred compounds of the invention are those for which, in the formula (I):

A represents phenyl, n and p represent 0, Z represents a bond and R$_3$ represents a hydrogen atom, or A represents phenyl, n represents 1 and E represents —CO—NR$_4$—, and more particularly those for which p represents 1, R$_1$ and R$_2$ represent a hydrogen atom and Z represents a bond; or A represents phenyl, n represents 1, E represents —SO$_2$—NR$_4$—; or A represents phenyl, n is equal to 1, E represents —CO—NR$_4$—, p is equal to 0 and Z represents —SO$_2$—NH—; or A represents an aromatic heterocycle such as benzothienyl or thienyl; or A represents naphthyl; or n represents 1 and E represents an oxygen atom.

Another group of preferred compounds consists of the compounds of formula:

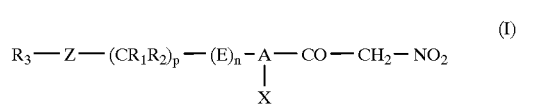

(I)

in which

A represents phenyl, naphthyl, benzothienyl or thienyl;

X represents halogen, cyano, $C_1$–$C_7$ alkyl, trifluoromethyl, $C_2$–$C_7$ alkoxy or trifluoromethoxy;

R$_1$ and R$_2$ represent a hydrogen atom, or R$_1$ and R$_2$ together form an alkylene chain of the —(CH$_2$)$_r$— type, where r is chosen from 2, 3 and 4;

p is chosen from 0, 1, 2 and 3;

Z represents a bond, the divalent radical —CO—NH— in which the carbonyl function is linked to $R_3$ or the divalent radical —$SO_2$—NH— in which the sulfonyl function is linked to $R_3$;

$R_3$ represents a hydrogen atom, $C_1$–$C_7$ alkyl optionally substituted with one or more identical or different Y radicals; phenyl optionally substituted with one or more identical or different Y radicals; phenoxy optionally substituted with one or more identical or different Y radicals; $C_3$–$C_{12}$ cycloalkyl optionally substituted with one or more identical or different Y radicals; benzothienyl; benzofuryl; or $R_3$ represents 1,3-dihydro-1,3-dioxo-2H-isoindol-2-yl or 2-oxopiperidinyl;

Y represents a halogen atom, $C_1$–$C_7$ alkoxy, trifluoromethyl, carboxy, trifluoromethoxy or phenyl;

E represents a divalent radical chosen from:
 (i) —CO—$NR_4$ in which the carbonyl group is linked to —$(CR_1R_2)_p$— and $R_4$ represents the radical $(CH_2)_q$—$R_5$ where q is chosen from 0 and 1, and where $R_5$ represents a hydrogen atom, a $C_1$–$C_7$ alkyl group or a phenyl group;
 (ii) —$SO_2$—$NR_4$— in which the sulfonyl group is linked to —$(CR_1R_2)_p$— and $R_4$ is as defined above;
 (iii) —$NR_4$— in which $R_4$ is as defined above;
 (iv) —CH=N— in which the nitrogen atom is linked to A; and
 (v) a hydrogen atom;

n represents 0 or 1;
 on the condition that —A(X)—(E)$_n$—$(CR_1R_2)_p$—Z—$R_3$ does not represent halophenyl, methylphenyl, dichlorophenyl, dimethylphenyl, 4-ethoxy-2-methylaminophenyl, methylindolyl, dimethylindolyl, 2-hydroxyphenyl substituted with a group X, 2-methoxyphenyl substituted with a group X and optionally substituted, 2-fluorophenyl as defined above, and
 on the condition that when A represents pyridyl, X represents methyl and n is equal to 1, E does not represent —$NR_4$—, as well as their addition salts with pharmaceutically acceptable bases.

Among the preferred compounds of the invention, there may be mentioned:
(1) nitromethyl 2-trifluoromethoxyphenyl ketone;
(2) nitromethyl 2-cyanophenyl ketone;
(3) nitromethyl 2-ethylphenyl ketone;
(4) nitromethyl 2-trifluoromethylphenyl ketone;
(5) nitromethyl 2-ethoxyphenyl ketone;
(6) nitromethyl 2-isopropyloxyphenyl ketone;
(7) nitromethyl 2-methyl-1-naphthyl ketone;
(8) nitromethyl 3-chloro-2-naphthyl ketone;
(9) nitromethyl 3-chlorobenzo[b]thien-2-yl ketone;
(10) nitromethyl 6-methoxy-5-trifluoromethyl-1-naphthyl ketone;
(11) 4-methyl-N-[2-nitromethylcarbonyl-3-methylbenzo[b]thien-5-yl]benzenesulfonamide;
(12) N-[3-chloro-4-nitromethylcarbonylphenyl]acetamide;
(13) nitromethyl 4-amino-2-chlorophenyl ketone;
(14) N-[3-chloro-4-nitromethylcarbonylphenyl]benzamide;
(15) N-[3-chloro-4-nitromethylcarbonylphenyl]-4-chlorobenzamide;
(16) N-[3-chloro-4-nitromethylcarbonylphenyl]-4-methylbenzamide;
(17) N-[3-chloro-4-nitromethylcarbonylphenyl]-4-methoxybenzamide;
(18) N-[3-chloro-4-nitromethylcarbonylphenyl]-2-trifluoromethylbenzamide;
(19) N-[3-chloro-4-nitromethylcarbonylphenyl]-2,2,3,3-tetramethylcyclopropanecarboxamide;
(20) N-[3-chloro-4-nitromethylcarbonylphenyl] hexaneamide;
(21) N-[3-chloro-4-nitromethylcarbonylphenyl] cyclopentylacetamide;
(22) N-[3-chloro-4-nitromethylcarbonylphenyl]-3-phenylpropaneamide;
(23) N-[3-chloro-4-nitromethylcarbonylphenyl]-2-phenylpropaneamide;
(24) N-[3-chloro-4-nitromethylcarbonylphenyl] phenylacetamide;
(25) N-[3-chloro-4-nitromethylcarbonylphenyl]benzo[b]-thienyl-2-carboxamide;
(26) N-[3-chloro-4-nitromethylcarbonylphenyl]benzofuryl-2-carboxamide;
(27) N-[3-chloro-4-nitromethylcarbonylphenyl]-4-chlorophenoxyacetamide;
(28) 2-chloro-N-[3-chloro-4-nitromethylcarbonylphenyl] phenylacetamide;
(29) N-[3-chloro-4-nitromethylcarbonylphenyl]-1-(4-chlorophenyl)cyclopropylcarboxamide;
(30) N-[3-chloro-4-nitromethylcarbonylphenyl]-2-trifluoromethylphenylacetamide;
(31) N-[3-chloro-4-nitromethylcarbonylphenyl]-4-chlorobenzenesulfonamide;
(32) N-[3-chloro-4-nitromethylcarbonylphenyl] benzenesulfonamide;
(33) nitromethyl 4-[N,N-di(phenylmethyl)amino]-2-chlorophenyl ketone;
(34) N-[2-chloro-3-nitromethylcarbonylphenyl]acetamide;
(35) N-[2-chloro-3-nitromethylcarbonylphenyl]-2-methylphenylacetamide;
(36) N-[4-chloro-3-nitromethylcarbonylphenyl]acetamide;
(37) N-[4-chloro-3-nitromethylcarbonylphenyl]-2-methylphenylacetamide;
(38) N-[4-chloro-3-nitromethylcarbonylphenyl] benzenesulfonamide;
(39) 2-[3-chloro-4-nitromethylcarbonylphenylaminocarbonylmethylaminocarbonyl]benzoic acid;
(40) N-[3-chloro-4-nitromethylcarbonylphenyl]-1,3-dihydro-1,3-dioxo-2H-isoindol-2-ylacetamide
(41) 1-[3-chloro-4-nitromethylcarbonylphenyl]-3-phenylsulfonylurea;
(42) nitromethyl 3-methyl-2-thienyl ketone;
(43) N-[3-chloro-4-nitromethylcarbonylphenyl]-2-methylphenylacetamide;
(44) N-[3-chloro-4-nitromethylcarbonylphenyl]-2-oxopiperidine;
(45) N-[3-chloro-4-nitromethylcarbonylphenyl]-1-(4-chlorophenyl)cyclopentanecarboxamide;
(46) N-[3-chloro-4-nitromethylcarbonylphenyl]indan-2-ylacetamide;
(47) N-[3-chloro-4-nitromethylcarbonylphenyl]-4-chlorophenylacetamide;
(48) N-[3-chloro-4-nitromethylcarbonylphenyl]-3-chlorophenylacetamide;
(49) N-[3-chloro-4-nitromethylcarbonylphenyl]-3,4-dichlorophenylacetamide;
(50) N-[3-chloro-4-nitromethylcarbonylphenyl]-4-methylphenylacetamide;
(51) N-[3-chloro-4-nitromethylcarbonylphenyl]-3-methylphenylacetamide;
(52) N-[3-chloro-4-nitromethylcarbonylphenyl]-3,4-dimethylphenylacetamide;

(53) N-[3-chloro-4-nitromethylcarbonylphenyl]-4-trifluoromethylphenylacetamide;
(54) N-[3-chloro-4-nitromethylcarbonylphenyl]-4-methoxyphenylacetamide;
(55) N-[3-chloro-4-nitromethylcarbonylphenyl]-4-nitrophenylacetamide;
(56) N-[3-chloro-4-nitromethylcarbonylphenyl]-2-fluoro-4-bromophenylacetamide;
(57) N-[3-chloro-4-nitromethylcarbonylphenyl]-4-fluorophenylacetamide;
(58) N-[3-chloro-4-nitromethylcarbonylphenyl]-3-phenyl-2-propeneamide;
(59) N-[3-methyl-4-nitromethylcarbonylphenyl]-2-methylphenylacetamide;
(60) N-[2-bromo-4-nitromethylcarbonylphenyl]-2-methylphenylacetamide;
(61) nitromethyl 2-chloro-4-methoxyphenyl ketone;
(62) nitromethyl 2-isopropylphenyl ketone;
(63) N-[4-chloro-2-nitromethylcarbonylphenyl]-2-methylphenylacetamide;
(64) nitromethyl 2-chloro-4-phenylthiophenyl ketone;
(65) N-[3-chloro-4-nitromethylcarbonylphenyl]-4-[3-chloro-4-nitromethylcarbonylphenylaminocarbonyl]-3-phenylbutaneamide;
(66) nitromethyl 2-chloro-4-phenylsulfinylphenyl ketone;
(67) nitromethyl 4-chloro-2-trifluoromethoxyphenyl ketone;
(68) N-[2-(3-chloro-4-nitromethylcarbonylphenylethyl)]-2-methylbenzenesulfonamide;
(69) N-[3-bromo-4-nitromethylcarbonylphenyl]-2-methylphenylacetamide;
(70) N-[3-chloro-4-nitromethylcarbonylphenyl]-N-isopropylbenzenesulfonamide.

The compounds of the invention are for example prepared according to the following methods (A) and (B):

(A) The products of formula (I) may be prepared from the carboxylic acids (II)

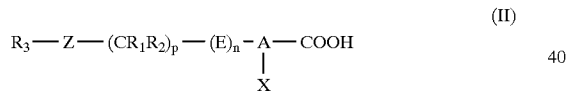

by the action of di-($C_1$–$C_7$)alkyl cyanophosphonate and nitromethane in the presence of a base in a solvent which is inert towards the reaction, preferably in a polar aprotic solvent such as dimethylformamide or tetrahydrofuran. Advantageously, the molar ratio of the carboxylic acid of formula (II) to the nitromethane varies between 0.6/1 and 2/1, preferably between 0.8/1 and 1.2/1. As base, use is preferably made of an amine, an alkyllithium, an alkali metal hydride, an alkali metal carbonate, an alkali metal hydroxide or an alkali metal alcoholate and especially triethylamine, pyridine, butyllithium, sodium hydride, potassium carbonate, potassium hydroxide or potassium tertbutoxide in a ratio of the carboxylic acid of formula (II) to the base of between 0.2/1 and 0.5/1, or better still in a ratio of 0.4/1.

The reaction temperature is generally between −78° C. and the reflux temperature of the solvent and preferably between −5° C. and 80° C. Generally, the reaction is continued for 2 to 72 hours, preferably for 2 to 18 hours.

(B) As a variant, the product of formula (I) may be prepared from the carboxylic acids of formula (II) by prior conversion to the phenyl ester of formula (III) according to the following reaction scheme:

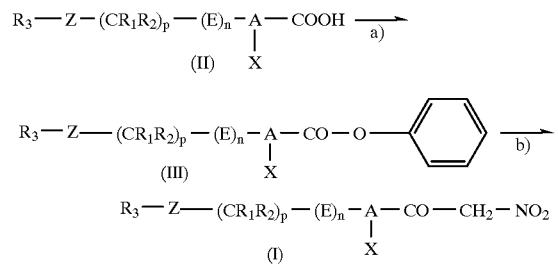

a) The preparation of the phenyl esters (III) may be carried out by reacting successively or simultaneously $SOCl_2$, or $POCl_3$, and phenol in the absence or in the presence of a solvent which is inert towards the reaction. When a solvent is used, it is preferably an aprotic solvent such as dichloromethane, benzene or toluene. In this first step, the molar ratio of $SOCl_2$, respectively $POCl_3$, to the carboxylic acid of formula (II) is preferably between 1/1 and 50/1, or better still the ratio is 10/1. Likewise, it is preferable that the molar ratio of the carboxylic acid to the phenol is between 1/0.9 and 1/1.2, or better still this ratio is 1/1.05. The reaction temperature is advantageously between −78° C. and the reflux temperature of the solvent, preferably between 0° C. and the reflux temperature of the solvent. This reaction is continued for 1 to 48 hours, preferably for 1 to 8 hours.

b) The phenyl esters of formula (III) thus formed are then treated with nitromethane in the presence of a base at a temperature of between 20° C. and the boiling point of the solvent and, preferably, between 20° C. and 40° C. The duration of the reaction varies advantageously between 2 and 72 hours, preferably between 2 and 48 hours. For this stage, the molar ratio of the compound of formula (III) to the nitromethane will be set at between 1/1 and 1/5, this ratio being preferably equal to 1/3. As appropriate base, there will be used for example an alkali metal hydroxide, an alkali metal carbonate, an alkali metal hydride, an alkyllithium, an amine or an alkali metal alcoholate. Thus, the base may be, for example, selected from potassium tert-butoxide, sodium hydroxide, potassium hydroxide, potassium carbonate, sodium hydride, butyllithium and pyridine. The molar ratio of the phenyl ester of formula (III) to the base will be advantageously between 1/1 and 1/5, this ratio being preferably equal to 1/3.

Other procedures allow the preparation of the compounds of formula (I).

When in the formula (I) above, n is equal to 1 and E represents —CO—$NR_4$—, the compounds of the invention may be obtained by reacting an acid halide of formula $R_3$—Z—$(CR_1R_2)_p$—CO—hal where $R_1$, $R_2$, $R_3$, Z and p are as defined above and hal is a halogen atom, with an amine of formula (IV):

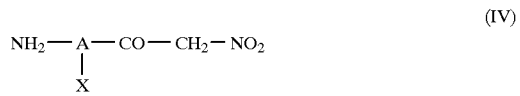

in which A and X are as defined above.

The procedure is carried out in the presence of a base, preferably an amine, such as pyridine, triethylamine or dimethylaminopyridine, in a solvent, preferably an aprotic solvent, at a temperature of between −20° C. and the reflux temperature of the solvent, for example between 0 and 40° C. The duration of the reaction is between 2 and 48 hours.

Examples of preferred solvents are dichloro-methane, tetrahydrofuran, benzene or toluene.

When, in the formula (I) above, n is equal to 1 and E represents —$SO_2$—$NR_4$—, the compounds of the invention may be obtained by reacting a sulfonyl halide of formula $R_3$—Z—$(CR_1R_2)_p$—$SO_2$—hal where $R_1$, $R_2$, $R_3$, Z and p are as defined above and hal is a halogen atom, with an amine of formula (IV) as defined above. Here again, the procedure is advantageously carried out in the presence of a base in a solvent at a temperature of between −20° C. and the reflux temperature of the solvent. The preferred operating conditions are the same as for the reaction of the acid chloride with the amine of formula (IV) above.

As a variant, it is possible, in a first instance, to synthesize the benzyl ester of formula (III):

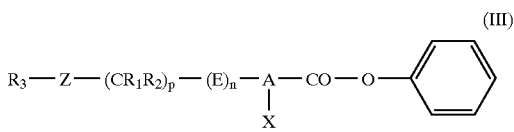

(III)

according to one of the reaction steps (i) to (vi) below, and then to treat the benzyl ester of formula (III) by the action of nitromethane in the presence of a base as described above:

step (i) when n is equal to 1 and E represents —CO—$NR_4$—, an acid halide of formula $R_3$—Z—$(CR_1R_2)_p$—CO—hal, where $R_1$, $R_2$, $R_3$, Z and p are as defined above and hal is a halogen atom, is reacted with an amine of formula (V):

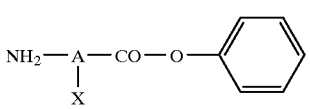

(V)

in which A and X are as defined above; or step (ii) when n is equal to 1 and E represents —$SO_2$—$NR_4$—, a sulfonyl halide of formula $R_3$—Z—$(CR_1R_2)_p$—$SO_2$—hal, where $R_1$, $R_2$, $R_3$, Z and p are as defined above and hal is a halogen atom, is reacted with an amine of formula (V) as defined above; or step (iii) when n is equal to 1 and E represents —$NR_4$—, a compound of formula $R_3$—Z—$(CR_1R_2)_p$—hal, where $R_1$, $R_2$, $R_3$, Z and p are as defined above and hal is a halogen atom, is reacted with an amine of formula (V) as defined above; or step (iv) when n is equal to 1 and E represents —CH=N—, an aldehyde of formula $R_3$—Z—$(CR_1R_2)_p$—CHO, where $R_1$, $R_2$, $R_3$, Z and p are as defined above, is reacted with an amine of formula (V) as defined above; or step (v) when n is equal to 1 and E represents —O—, a compound of formula $R_3$—Z—$(CR_1R_2)_p$—hal, where $R_1$, $R_2$, $R_3$, Z and p are as defined above and hal is a halogen atom, is reacted with an alcohol of formula (VI):

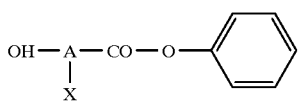

(VI)

in which A and X are as defined above;

step (vi) when n is equal to 1, E represents —CO—$NR_4$—, p is 0 and Z represents —$SO_2$—NH—, an isocyanate of formula $R_3$—$SO_2$—N=C=O, in which $R_3$ is as defined above, is reacted with an amine of formula (V) as defined above;

step (vii) when n is equal to 1 and E represents —CO—$NR_4$—, an acid of formula $R_3$—Z—$(CR_1R_2)_p$—COOH, where $R_1$, $R_2$, $R_3$, Z and p are as defined above, is reacted with an amine of formula (V) as defined above.

Some compounds of formula (I) may be obtained from compounds of formula (I) using simple conversion steps.

Thus, the compounds of formula (I) in which n is equal to 1, E represents —CO—NH—, p represents 1, $R_1$ and $R_2$ represent a hydrogen atom, Z represents a bond and $R_3$ represents 1,3-dihydro-1,3-dioxo-2H-isoindol-2-yl may be prepared from the corresponding compounds (having meanings of A and X which are identical) in which n is equal to 1, E represents —CO—NH—, p represents 1, $R_1$ and $R_2$ represent a hydrogen atom, Z represents —CO—NH— and $R_3$ represents 2-carboxyphenyl, by the action of hydrochloric acid.

Likewise, the compounds in which n represents 1, E represents —CO—NH—, —$(CR_1R_2)_p$— represents $CH_2$ and $R_3$ represents 2-[(4-nitromethylcarbonyl-3-chlorophenyl)-aminocarbonyl]-1-(phenyl)ethyl may be prepared by reacting the dichloride of formula

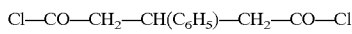

with two equivalents of the ester of formula

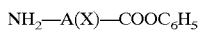

in the presence of a base, and then treating the compound obtained with nitromethane in the presence of a base.

The compounds of formula (IV) are easily synthesized from commercially available compounds by methods known in the art.

By way of example, the compounds of formula (IV) may be obtained from the corresponding amines of formula (VII):

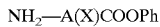

(VII)

according to a procedure comprising the steps consisting of:

protecting the amino function with a protective group such as a ($C_1$-$C_7$)alkylcarbonyl group,. for example acetyl;

reacting the amine thus protected with di($C_1$-$C_7$)alkyl cyanophosphonate and nitromethane in the presence of a base; and then deprotecting the amino function, for example by the action of sodium hydroxide when the protective group is an acetyl group.

The capacity of the compounds of the invention to inhibit the enzyme aldose reductase and to prevent the accumulation of sorbitol may be demonstrated during standard laboratory tests below:

1) Study in vitro: inhibition of aldose reductase

The aldose reductase used is obtained from male Wistar rat crystalline lenses according to a modification of the method of S. HAYMAN et al. (Journal of Biological Chemistry 240, p. 877, 1965). The enzymatic extract is diluted in a phosphate buffer in the presence of NADPH and various concentrations of the test products. The reaction is initiated with L-glyceraldehyde and the reaction rate is measured by monitoring the disappearance of NADPH by spectrophotometry at 340 nm. The reaction rate is calculated for each product concentration and then the concentration necessary for a 50% reduction in the reaction rate ($IC_{50}$) is evaluated by linear interpolation. The results are presented in Table 1 below.

2) Study in vivo: reduction of sorbitol accumulation 200 to 250 g male Wistar rats are made diabetic by intravenous injection of streptozotocin (60 mg/kg). They then receive an oral treatment of the test products, in the form of a suspension, 4 hours, 30 hours and 52 hours after the injection of streptozotocin. Eighteen hours after the last oral treatment, the rats are stunned and decapitated and then their sciatic nerves are removed. After extraction, the sorbitol level in the nerves is measured according to the enzymatic method described by H. U. BERGMEYER (Methods of enzymatic analysis. H. U. BERGMEYER ed., Academic Press New York 3, p. 1323, 1974).

The percentage protection is calculated for each product relative to the batch of diabetic animals taking into account the sorbitol level in the sciatic nerves of nondiabetic rats.

By way of example, the results obtained for some of the test products are given in the following table:

TABLE 1

| Example No. | Inhibition of aldose reductase in vitro $IC_{50}$ (nm) | Protection against increase in sorbitol after administration 10 mg/kg/d (%) |
| --- | --- | --- |
| 1 | 41 | 70 |
| 23 | 7 | 40 |
| 24 | 7 | 45 |
| 28 | 7 | 58 |
| 30 | 7 | 61 |
| 43 | 7 | 70 |
| 59 | 6 | 52 |

The compounds of the invention may be used by way of medicaments as aldose reductase inhibitors, and are especially useful in the treatment of the complications of diabetes such as cataracts, retinopathies, neuropathies, nephropathies and certain vascular diseases. The daily dosages may vary from 5 mg to 200 mg of active ingredient, for example.

These medicaments may be administered by the oral route in the form of tablets, gelatin capsules or granules affording immediate release or controlled release, by the intravenous route in the form of an injectable solution, by the transdermal route in the form of an adhesive transdermal device, by the local route in the form of a collyrium, solution, cream or gel.

A solid medicament for oral administration containing a compound of the present invention as active ingredient is prepared by supplementing the said compound with a filler and, where appropriate, a binder, a disintegrating agent, a lubricant, a coloring or a taste enhancer, and by forming the mixture into a tablet, a coated tablet, a granule, a powder or a capsule.

Examples of a filler comprise lactose, maize starch, sucrose, glucose, sorbitol, crystalline cellulose and silicon dioxide, and examples of a binder comprise poly(vinyl alcohol), poly(vinyl ether), ethyl cellulose, methyl cellulose, acacia, tragacanth gum, gelatin, shellac, hydroxypropylcellulose, hydroxypropylmethylcellulose, calcium citrate, dextrin and pectin. Examples of lubricants comprise magnesium stearate, talc, poyethylene glycol, silica and hardened vegetable oils. The coloring may be any of those permitted for use in medicaments. Examples of taste enhancers comprise cocoa powder, mint in herb form, aromatic powder, mint in oil form, borneol and cinnamon powder. Of course, the tablet or granule may be suitably coated with sugar, gelatin and the like.

An injectable form containing the compound of the present invention as active ingredient is prepared, where appropriate, by mixing the said compound with a pH regulator, a buffering agent, a suspending agent, a solubilizing agent, a stabilizer, a tonic agent and/or a preservative, and by converting the mixture to a form injectable by the intravenous, subcutaneous or intramuscular route, according to a conventional process. Where appropriate, the injectable form obtained may be freeze-dried by a conventional process.

Examples of suspending agents comprise methyl cellulose, polysorbate 80, hydroxyethylcellulose, acacia, tragacanth gum powder, sodium carboxymethylcellulose and polyethoxylated sorbitan monolaurate.

Examples of a solubilizing agent comprise castor oil solidified with polyoxyethylene, polysorbate 80, nicotinamide, polyethoxylated sorbitan monolaurate and the ethyl ester of castor oil fatty acid.

In addition, the stabilizer comprises sodium sulfite, sodium metasulfite and ether, whereas the preservative comprises methyl p-hydroxybenzoate, ethyl p-hydroxybenzoate, sorbic acid, phenol, cresol and chlorocresol.

A few pharmaceutical formulations are given below by way of nonlimiting examples:

| | |
| --- | --- |
| ● Composition of an immediate-release tablet<br>Active ingredient<br>Excipients: lactose, wheat starch, polyvidone, talc, magnesium stearate. | 100 mg |
| ● Composition of a controlled-release tablet<br>Active ingredient<br>Excipients: lactose, polyvidone, talc, magnesium stearate, polymer (cellulose or acrylic and methacrylic or vinyl or glyceride derivative). | 100 mg |
| ● Composition of a gelatin capsule<br>Active ingredient<br>Excipients: lactose, wheat starch, talc, magnesium stearate. | 100 mg |
| ● Composition of an ampoule of injectable solution<br>Active ingredient<br>Excipients: mannitol, water for injection. | 200 mg |
| ● Composition of a cream<br>(composition per 100 g of cream)<br>Active ingredient<br>Excipients: self-emulsifiable cetylstearyl alcohol cetylaryloctanoate, nipasol, sorbic acid, propylene glycol, carbapol. | 2 g |
| ● Composition of a collyrium<br>Active ingredient<br>Excipients: sodium chloride, benzalkonium chloride, water for injection. | 15 mg |

The following examples illustrate the invention with no limitation being implied.

In the nuclear magnetic resonance (NMR) data, the following abbreviations are used: s for singlet, d for doublet, t for triplet, q for quadruplet and m for unresolved complex; the chemical shifts δ are expressed in ppm; m.p.=represents the melting point and b.p. the boiling point.

The entire disclosure of all applications, patents and publications, cited above and below, and of corresponding European application No. 97108369.6, filed May 23, 1997, is hereby incorporated by reference.

EXAMPLE 1

Nitromethyl 2-trifluoromethoxyphenyl ketone a) Phenyl 2-(trifluoromethoxyphenyl)benzoate A mixture composed of 10 g (48.5 mmol) of 2-(trifluoromethoxy)benzoic acid, 50 ml of thionyl chloride and a drop of dimethylformamide is heated under reflux for 1.5 hours. After cooling and concentrating the reaction mixture under vacuum, a residue is obtained which is stirred for 2 hours at 100° C. in the presence of 4.75 g (50 mmol) of phenol. After cooling, the reaction medium is taken up in dichloromethane, washed with a saturated $NaHCO_3$ solution and then with water, dried over $Na_2SO_4$ and concentrated.

After distillation, 11 g of a colorless liquid are obtained (yield=80%).

b.p.=100–110° C. (under 1 mm of Hg); NMR ($CDCl_3$): 7.15–7.4 (7H, m); 7.55 (1H, m); 8.05 (1H, dd, J=7.8 Hz and 1.8 Hz)

b) Nitromethyl 2-trifluoromethoxyphenyl ketone 4.2 ml (75 mmol) of nitromethane are added to a solution composed of 8.5 g (75 mmol) of potassium tertbutoxide and 115 ml of dimethyl sulfoxide, maintained at 15° C. The mixture is stirred for 1 hour at 15° C. before adding, dropwise, 7 g (25 mmol) of the phenyl ester obtained in step a) above. After stirring for 3 hours at 15–20° C., 68 ml of ice-cold water and 6.8 ml of concentrated hydrochloric acid are added, with stirring, before pouring into 500 ml of an ice-water mixture. The precipitate formed is drained, washed with water and with hexane, before being dried. After recrystallization from an ethyl acetate-hexane mixture, 3 g of a cottony white solid are obtained (yield=48%).

m.p.=35–36° C.; NMR (DMSO-$d_6$): 6.3 (2H, s, exchangeable with $CF_3COOD$); 7.55 (2H, m); 7.8 (1H, m); 7.95 (1H, dd, J=7.7 Hz and 1.6 Hz).

EXAMPLES 2 to 6

By carrying out the procedure as in Example 1 (a and b), Examples 2 to 6 are obtained:

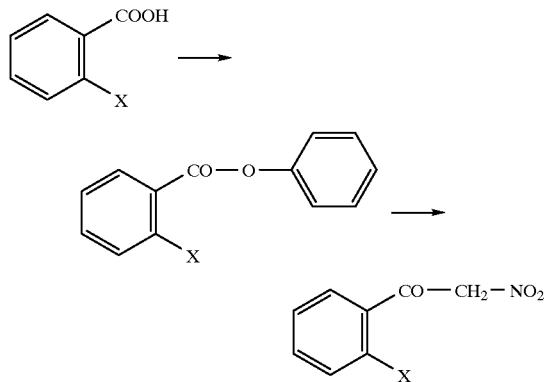

Nitromethyl 2-cyanophenyl ketone (Example 2)
Nitromethyl 2-ethylphenyl ketone (Example 3)
Nitromethyl 2-trifluoromethylphenyl ketone (Example 4)
Nitromethyl 2-ethoxyphenyl ketone (Example 5)
Nitromethyl 2-isopropyloxyphenyl ketone (Example 6)

| Examples | X | Phenyl esters | Compounds —CO—$CH_2NO_2$ |
|---|---|---|---|
| 2 | —CN | J. Am. Chem. Soc. (1962) 2196–2201 | m.p.=147–149° C. NMR(DMSO-$d_6$): 6.75 (2H, s, exchangeable with $CF_3COOD$); 8.1(2H, m); 8.3(2H, m) |
| 3 | —$CH_2CH_3$ | b.p.$_{1.2}$=105–115° C. NMR($CDCl_3$): 1.2(3H, t, J=7.5Hz); 3.0(2H, q, J=7.5Hz); 7.1–7.3(5H, m); 7.35–7.45(3H, m); 8.05(1H, dd, J=6.6Hz and 1.3Hz) | m.p.=62–63° C. NMR(DMSO-$d_6$): 1.15(3H, t, J=7.45Hz); 2.85(2H, q, J=7.45Hz); 6.45(2H, s, exchangeable with $CF_3COOD$); 7.40(2H, m); 7.6 (1H, m); 7.7(1H, dd, J=7.75Hz and 1.15Hz) |
| 4 | —$CF_3$ | NMR($CDCl_3$): 7.1(3H, m); 7.3(2H, m); 7.55(2H, m); 7.7(1H, m); 7.8(1H, m) | m.p=55–57° C. NMR($CDCl_3$): 5.9(2H, s, exchangeable with $CF_3COOD$); 7.75(1H, m); 7.9(2H, m); 8.0(1H, m) |
| 5 | —$OCH_2CH_3$ | CA 95 168816 f | m.p=145–148° C. NMR(DMSO-$d_6$): 1.6(3H, t, J=7Hz); 4.35(2H, q, J=7Hz); 6.25(2H, s, exchangeable with $CF_3COOD$); 7.25(1H, m); 7.35(1H, m); 8.15(1H, m); 8.0(1H, m) |
| 6 | —$OCH(CH_3)_2$ | b.p.$_{0.5}$=150° C. NMR($CDCl_3$): 1.3(6H, d, J=6.1Hz); 4.6(1H, m, J=6.1Hz); 6.95(2H, m); 7.15(3H, m); 7.35(3H, m); 7.85(1H, dd, J=7.7Hz and 1.8Hz) | m.p.=78–80° C. NMR(DMSO-$d_6$): 1.4 (6H, d; J=6Hz); 4.9(1H, m, J=6Hz); 6.1(2H, s, exchangeable with $CF_3COOD$); 7.1(1H, m); 7.2(1H, d, J=8.45Hz); 7.7(1H, m); 7.9(1H, dd, J=7.85Hz and 1.8Hz) |

EXAMPLES 7 to 9

By carrying out the procedure as in Example 1 (a and b), the compounds of Examples 7 to 9 are obtained:

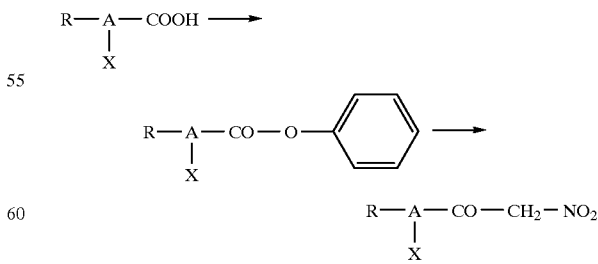

where R represents $R_3$—Z—$(CR_1R_2)_p$—$(E)_n$—

Nitromethyl 2-methyl-1-naphthyl ketone (Example 7)

Nitromethyl 3-chloro-2-naphthyl ketone (Example 8)
Nitromethyl 3-chlorobenzo[b]thien-2-yl ketone (Example 9)

| Examples | R—A—X | Phenyl esters | Compounds —CO—CH$_2$NO$_2$ |
|---|---|---|---|
| 7 | (1-methyl-2-naphthyl) | m.p.=65–69° C. NMR(CDCl$_3$): 1.6(3H, s); 7.2–7.5(8H, m); 7.8(2H, m); 7.95(1H, m) | m.p.=126–128° C. NMR(CDCl$_3$): 2.5(3H, s); 5.9(2H, s, exchangeable with CF$_3$COOD); 7.4(2H, m); 7.7(2H, m); 8.0(1H, m); 8.6(1H, d, J=0.5Hz) |
| 8 | (3-chloro-2-methylnaphthyl) | NMR(DMSO-d$_6$): 7.3(3H, m); 7.5(2H, m); 7.7(2H, m); 8.0(1H, d, J=8.1Hz); 8.15(1H, d, J=8Hz); 8.2(1H, s); 8.8(1H, s) | m.p.=109–113° C. NMR(DMSO-d$_6$): 6.6(2H, s, exchangeable with CF$_3$COOD); 7.7(2H, m); 8.0(2H, m); 8.25(1H, s); 8.65(1H, s) |
| 9 | (3-chloro-2-methylbenzothien-yl) | Z. Chem (1997) 17,133–134 | m.p.=158–160° C. NMR(DMSO-d$_6$): 6.65(2H, s, exchangeable with CF$_3$COOD); 7.8(2H, m); 8.15(1H, dd, J=7.9Hz and 0.8Hz; 8.3(1H, d, J=7.9Hz) |

EXAMPLES 10 and 11

By carrying out the procedure as in Example 1 (a and b), the compounds of Examples 10 and 11 are obtained:

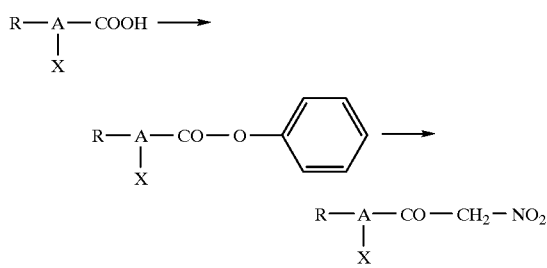

where R represents R$_3$—Z—(CR$_1$R$_2$)$_p$—(E)$_n$—

Nitromethyl 6-methoxy-5-trifluoromethyl-1-naphthyl ketone (Example 10)
4-Methyl-N-[2-nitromethylcarbonyl-3-methylbenzo[b]-thien-5-yl]benzenesulfonamide (Example 11)

| Examples | R—A—X | Phenyl esters | Compounds —CO—CH$_2$NO$_2$ |
|---|---|---|---|
| 10 | (6-methoxy-5-trifluoromethyl-1-naphthyl) | m.p. 137–139° C. NMR(DMSO-d$_6$): 4.1(3H, 3); 7.3–7.5(3H, m); 7.6(2H, m); 7.85(2H, m); 8.4(2H, m); 9.1(1H, d, J=9.75Hz) | m.p. 146–148° C. NMR(DMSO-d$_6$): 4.05(2H, s); 6.6(2H, s); 6.6(2H, s, exchangeable with CF$_3$COOD); 7.8(2H, m); 8.15(1H, d, J=7Hz) 8.35(1H, m); 8.85(1H, d, J=9.75Hz) |
| 11 | (4-methyl-N-[3-methylbenzo[b]thien-5-yl]benzenesulfonamide) | NMR(DMSO-d$_6$) 2.35(3H, s); 2.7(3H, s); 2.7(3H, s); 6.8(4H, m); 7.1–7.6(5H, m); 7.9(2H, m); 8.0(1H, m); 10.5(1H, s, exchangeable with CF$_3$COOD) | m.p. 185–190° C. NMR(DMSO-d$_6$): 2.3(3H, s); 2.6(3H, s); 6.45(2H, s exchangeable with CF$_3$COOD); 7.3(3H, m)7.7(3H, m); 7.9(1H, d, J=8.75Hz); 10.45(1H, s, exchangeable with CF$_3$COOD) |

EXAMPLE 12

N-[3-Chloro-4-nitromethylcarbonylphenyl]acetamide a) Phenyl 4-amino-2-chlorobenzoate 30 g of phenyl 2-chloro-4-nitrobenzoate prepared according to Makoto Suzuki, Yakugaku Zasshi (1959) 79, 286–90 (CA 53 14991 f) are added to a mixture of 800 ml of water, 60 ml of acetic acid and 96.5 g (1.728 mol) of iron. The reaction medium is heated for 1 hour under reflux. After cooling, the reaction medium is filtered and the solid recovered is washed with ethyl acetate. The aqueous phase is saturated with NaCl before being extracted with ethyl acetate. The combined organic phases are concentrated and purified by chromatography on a silica column with CH$_2$Cl$_2$ (yield=82%).

m.p.=127–128° C.; NMR (DMSO-d$_6$): 6.35 (2H, s, exchangeable with CF$_3$COOD); 6.55 (1H, dd, J=8.6 Hz and 2.2 Hz); 6.7 (1H, d, J=2.2 Hz); 7.1–7.3 (3H, m); 7.45 (2H, m); 7.9 (1H, d, J=8.6 Hz).

b) Phenyl 4-(acetylamino)-2-chlorobenzoate 37 ml (266 mmol) of triethylamine are added to a mixture composed of 60 g (242 mmol) of the amine obtained in step a) above and of 280 ml of dichloromethane, followed by 20.6 ml (290 mmol) of acetyl chloride. After stirring for 2 hours at room temperature, the medium is heated for 2 hours under reflux. After cooling, the reaction medium is thrown over an icehydrochloric acid mixture. The organic phase is decanted off and the aqueous phase is extracted with dichloromethane. The combined organic phases are washed with water, dried over Na$_2$SO$_4$ and concentrated, to give an oil which crystallizes. (Yield=quantitative)

m.p.=84–86° C.; NMR (DMSO-d$_6$): 2.15 (3H, s); 7.35 (3H, m); 7.5 (2H, m); 7.7 (1H, dd, J=8.7 Hz and 2 Hz); 8.05 (1H, d, J=2 Hz); 8.2 (1H, d, J=8.7 Hz); 10.5 (1H, s, exchangeable with CF$_3$COOD).

c) N-[3-chloro-4-nitromethylcarbonylphenyl]acetamide

The title compound was obtained by carrying out the procedure as in Example lb from the compound prepared in the preceding step b).

m.p.=196° C. (decomposition); NMR (DMSO-$d_6$): 2.3 (3H, s); 6.55 (2H, s, exchangeable with $CF_3COOD$); 7.8 (1H, dd, J=8.7 Hz and 1.8 Hz); 8.1 (2H, m); 10.7 (1H, s, exchangeable with $CF_3COOD$).

EXAMPLE 13

Nitromethyl 4-amino-2-chlorophenyl ketone

A mixture of 12.2 g (47.5 mmol) of N-[3-chloro-4-nitromethylcarbonylphenyl]acetamide prepared in Example 12, 11 g (274 mmol) of sodium hydroxide pellets and 161 ml of water is heated at 80° C. for 1 hour. After cooling, the reaction medium is diluted with 900 ml of water and acidified to pH 5 by adding acetic acid. The precipitate formed is recovered, washed with water and air-dried before being recrystallized from ethyl acetate (Yield=27%).

m.p.=131–133° C.; NMR (DMSO-$d_6$): 6.1 (2H, s, exchangeable with $CF_3COOD$); 6.45 (3H, m, of which 2H are exchangeable with $CF_3COOD$); 6.55 (1H, d, J=2 Hz); 7.5 (1H, d, J=8.75 Hz).

EXAMPLE 14

N-[3-Chloro-4-nitromethylcarbonylphenyl] benzamide a) Phenyl 2-chloro-4-[(benzoyl)amino]benzoate A solution of 2.27 g (16.1 mmol) of benzoyl chloride in 30 ml of dichloromethane is added dropwise to a mixture composed of 4 g (16.1 mmol) of the compound prepared in Example 12a, of 2.26 ml (17.7 mmol) of triethylamine and 40 ml of dichloromethane, maintained at 0° C. The reaction medium is stirred for 1 hour at 0° C. and then for 48 hours at room temperature. The dichloromethane is evaporated off. The residue is taken up in water, the solid filtered, washed with water and dried under vacuum at 80° C., to give 5 g of an off-white powder (Yield=89%).

m.p.=126–128° C.; NMR (DMSO-$d_6$): 7.3 (3H, m); 7.5–7.7 (5H, m); 8.0 (3H, m); 8.2 (2H, m); 10.8 (1H, s, exchangeable with $CF_3COOD$).

b) N-[3-chloro-4-nitromethylcarbonylphenyl]benzoate

Obtained by carrying out the procedure as in Example 1b (Yield=57%).

m.p.=165–167° C.; NMR (DMSO-$d_6$): 6.6 (2H, s, exchangeable with $CF_3COOD$); 7.7–7.8 (3H, m); 8.1 (4H, m); 8.3 (1H, d, J=0.8 Hz); 10.9 (1H, s, exchangeable with $CF_3COOD$).

EXAMPLES 15 to 27

The compounds of Examples 15 to 27 were obtained from the amine prepared in Example 12a, the procedure being carried out as in Example 14.

N-[3-Chloro-4-nitromethylcarbonylphenyl]-4-chlorobenzamide (Example 15)

N-[3-Chloro-4-nitromethylcarbonylphenyl]-4-methylbenzamide (Example 16)

N-[3-Chloro-4-nitromethylcarbonylphenyl]-4-methoxybenzamide (Example 17)

N-[3-Chloro-4-nitromethylcarbonylphenyl]-2-trifluoromethylbenzamide (Example 18)

N-[3-Chloro-4-nitromethylcarbonylphenyl]-2,2,3,3-tetramethylcyclopropanecarboxamide (Example 19)

N-[3-Chloro-4-nitromethylcarbonylphenyl] cyclopentylacetamide (Example 20)

N-[3-Chloro-4-nitromethylcarbonylphenyl]hexaneamide (Example 21)

N-[3-Chloro-4-nitromethylcarbonylphenyl]-3-phenylpropaneamide (Example 22)

N-[3-Chloro-4-nitromethylcarbonylphenyl]-2-phenylpropaneamide (Example 23)

N-[3-Chloro-4-nitromethylcarbonylphenyl] phenylacetamide (Example 24)

N-[3-Chloro-4-nitromethylcarbonylphenyl]benzo[b]-thienyl-2-carboxamide (Example 25)

N-[3-Chloro-4-nitromethylcarbonylphenyl]benzofuryl-2-carboxamide (Example 26)

N-[3-Chloro-4-nitromethylcarbonylphenyl]-4-chlorophenoxyacetamide (Example 27).

| Examples | $R_3$—Z—$(CR_1R_2)_p$ | Phenyl esters | Compounds —CO—$CH_2NO_2$ |
|---|---|---|---|
| 15 | 4-chlorophenyl | m.p. 183–186° C. NMR (DMSO-$d_6$): 7.35(3H, m); 7.55(2H, m); 7.7(2H, d, J = 8.6Hz); 8.0(1H, dd, J = 8.7Hz and 2Hz); 8.05(2H, m); 8.25(2H, m); 10.8(1H, s, exchangeable with $CF_3COOD$) | m.p. 151–154° C. NMR (DMSO-$d_6$): 6.6(2H, s, exchangeable with $CF_3COOD$); 7.9(2H, d, J = 8.6Hz); 8.15(4H, m); 8.3(1H, d, J = 1.85Hz); 10.1(1H, s, exchangeable with $CF_3COOD$) |

-continued

| Examples | R3—Z— (CR₁R₂)ₚ | Phenyl esters | Compounds —CO—CH₂NO₂ |
|---|---|---|---|
| 16 | 4-methylphenyl (p-tolyl) | m.p. 151–152° C. NMR (DMSO-d₆): 2.45(3H, s); 7.35–7.55(7H, m); 8.0(3H, m); 8.25(2H, m); 10.7(1H, s, exchangeable with CF₃COOD) | m.p. 180–181° C. NMD (DMSO-d₆): 2.4(3H, s); 6.4(2H, s, exchangeable with CF₃COOD); 7.4(2H, d, J = 8Hz); 8.0(4H, m); 8.15(1H, d, J = 1.7Hz); 10.65 (1H, s, exchangeable with CF₃COOD) |
| 17 | 4-methoxyphenyl | m.p. 128–131° C. NMR (DMSO-d₆): 3.90(3H, s); 7.15(2H, d, J = 8.9Hz); 7.35(3H, m); 7.55(2H, m); 8.0(3H, m); 8.2(2H, m); 10.6(1H, s, exchangeable with CF₃COOD) | m.p. 189–190° C. NMR (DMSO-d₆): 3.95(3H, s); 6.5(2H, s, exchangeable with CF₃COOD); 7.2(2H, d, J = 8.8Hz); 8.05(4H, m); 8.25(1H, d, J = 1.7Hz); 10.7(1H, s, exchangeable with CF₃COOD) |
| 18 | 2-(trifluoromethyl)phenyl | m.p. 150–152° C. NMR (DMSO-d₆): 7.5(3H, m); 7.65(2H, m); 7.9–8.05(5H, m); 8.2(1H, d, J = 1.9Hz); 8.3(1H, d, J = 8.6Hz); 11.3(1H, s, exchangeable with CF₃COOD) | m.p. 199–201° C. NMR (DMSO-d₆): 6.7(2H, s, exchangeable with CF₃COOD); 8.0–8.3(7H, m); 11.4(1H, s, exchangeable with CF₃COOD) |
| 19 | 1,2,2,3,3-pentamethylcyclopropyl | NMR (DMSO-d₆): 1.2(6H, s); 1.25(6H, s); 7.3(3H, m); 7.5(2H, m); 7.6(1H, dd, J = 8.7Hz and 2.1Hz); 8.0(1H, d, J = 2.1Hz); 8.1(1H, d, J = 8.7Hz); 10.5(1H, s, exchangeable with CF₃COOD) | m.p. 94–96° C. NMR (DMSO-d₆): 1.25(6H, s); 13.0(6H, s); 1.4(1H, s); 6.45(2H, s, exchangeable with CF₃COOD); 7.65(1H, dd, J = 8.7 Hz and 2Hz); 7.95(1H, d, J = 8.7Hz); 8.05(1H, d, J = 2Hz); 10.2(1H, s, exchangeable with CF₃COOD) |
| 20 | H₃C—(CH₂)₄— | m.p. 60–63° C. NMR (DMSO-d₆): 0.95(3H, t, J = 6.8Hz); 1.35(4H, m); 1.7(2H, m); 2.4(2H, t, J = 7.35Hz); 7.35(3H, m); 7.55(2H, m); 7.7(1H, dd, J = 8.7Hz and 2Hz); 8.1(1H, d, J = 2Hz); 8.2(1H, d, J = 8.7Hz); 10.4(1H, s, exchangeable with CF₃COOD) | m.p. 80–83° C. NMR (DMSO-d₆): 0.90(3H, t, J = 6.8Hz); 1.35(4H, m); 1.65(2H, m); 2.4(2H, t, J = 7.3Hz); 6.45(2H, s, exchangeable with CF₃COOD); 7.7(1H, dd,) J = 8.7Hz and 1.8Hz); 7.95(1H, d, J = 8.7Hz); 8.0(1H, d, J = 1.8Hz); 10.5(1H, s, exchangeable with CF₃COOD) |

-continued

| Examples | R3—Z—(CR₁R₂)ₚ | Phenyl esters | Compounds —CO—CH₂NO₂ |
|---|---|---|---|
| 21 | 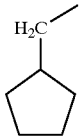 | NMR (DMSO-d₆): 1.1(2H, m); 1.45–1.7(6H, m); 2.15(1H, m); 2.3(2H, d), J = 7.3Hz); 7.25(3H, m); 7.4(2H, m); 7.6(1H, dd, J = 8.7Hz and 2.0Hz); 8.0(1H, d, J = 2.0Hz); 8.05(1H, d, (J = 8.7Hz); 10.3(1H, s, exchangeable with CF₃COOD) | m.p. 113–115° C. NMR (DMSO-d₆): 0.95(2H, m); 1.3(4H, m); 1.5(2H, m); 2.0(1H, m); 2.1(2H, d, J = 7.35Hz); 6.15(2H, s, exchangeable with CF₃COOD); 7.4(1H, dd, J = 8.7Hz and 2Hz); 7.7(2H, m); 10.2(1H, s, exchangeable with CF₃COOD) |
| 22 | 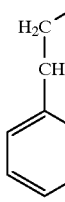 | NMR (DMSO-d₆): 2.7(2H, t, J = 7.7Hz); 2.95(2H, t, J = 7.7Hz); 7.3(8H, m); 7.5(2H, m); 7.65(1H, dd, J = 8.7Hz and 2Hz); 8.0(1H, d, J = 2Hz); 8.1(1H, d, J = 8.7Hz); 10.5(1H, s, exchangeable with CF₃COOD) | m.p. 122–123° C. NMR (DMSO-d₆): 2.7(2H, t, 2.9(2H, t, J = 7.7Hz); J = 7.7Hz); 6.4(2H, s, exchangeable with CF₃COOD); 7.25(5H, m); 7.6(1H, dd, J = 8.7Hz and 2Hz); 7.9(2H, m); 10.5(1H, s, exchangeable with CF₃COOD) |
| 23 | 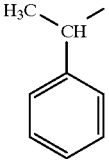 | NMR (DMSO-d₆): 1.45(3H, d, J = 7Hz); 3.9(1H, q, J = 7Hz); 7.3–7.5(10H, m); 7.7(1H, dd, J = 8.7Hz and 2Hz); 8.0(1H, d, J = 2Hz); 8.1(1H, d, J = 8.7Hz); 10.55(1H, s, exchangeable with CF₃COOD) | m.p. 136–137° C. NMR (DMSO-d₆): 1.4(3H, d, J = 7Hz); 3.85(1H, q, J = 7Hz); 6.4(2H, s, exchangeable with CF₃COOD); 7.3(5H, m); 7.6(1H, dd, J = 8.7Hz and 2Hz); 7.9(2H, m); 10.6(1H, s, exchangeable with CF₃COOD) |
| 24 | 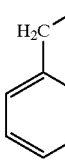 | m.p. 121–124° C. NMR (DMSO-d₆): 3.8(2H, s); 7.4(8H, m); 7.5(2H, m); 7.75(1H, dd, J = 8.7Hz and 2.05Hz); 8.1(1H, d, J = 2.05Hz); 8.2(1H, d, J = 8.7Hz); 10.8(1H, s, exchangeable with CF₃COOD) | m.p. 105–107° C. NMR (DMSO-d₆): 3.85(2H, s); 6.5(2H, s, exchangeable with CF₃COOD); 7.4–7.5(5H, m); 7.8(1H, dd, J = 8.7Hz and 2Hz); 8.1(2H, m); 10.9(1H, s, exchangeable with CF₃COOD) |
| 25 | 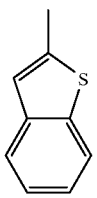 | m.p. 176° C. NMR (DMSO-d₆): 7.4(3H, m); 7.6(4H, m); 8.0(1H, dd, J = 8.7Hz and 2Hz); 8.15(2H, m); 8.25(2H, m); 8.5 (1H, s); 11.0(1H, s, exchangeable with CF₃COOD) | m.p. 210–211° C. NMR (DMSO-d₆): 6.43(2H, s, exchangeable with CF₃COOD); 7.5(2H, m); 7.9–8.2 (5H, m); 8.45(1H, s); 11.0(1H, s, exchangeable with CF₃COOD) |

-continued

| Examples | R3—Z—(CR₁R₂)ₚ | Phenyl esters | Compounds —CO—CH₂NO₂ |
|---|---|---|---|
| 26 | 2-methylbenzofuran structure | m.p. 186–188° C. NMR (DMSO-d₆): 7.35–7.60(7H, m); 7.8(1H, d, J = 8.4Hz); 7.95(2H, m); 8.1(1H, dd, J = 8.7Hz and 2Hz); 8.25(2H, m); 11.05(1H, s, exchangeable with CF₃COOD) | m.p. (199–200° C. NMR(DMSO-d₆): 6.45(2H, s, exchangeable with CF₃COOD); 7.4(1H, m); 7.55 (1H, m); 7.85(1H, m); 7.9(2H, m); 7.95(2H, m); 8.2(1H, s); 11.0 (1H, s, exchangeable with CFCOOD) |
| 27 | 4-chlorophenoxymethyl structure | m.p. 162–164° C. NMR (DMSO-d₆): 4.8(2H, s); 7.05(2H, m); 7.25–7.6(7H, m); 7.8(1H, m); 8.1(1H, d, J = 2Hz); 8.15(1H, d, J = 8.7Hz); 10.65(1H, s, exchangeable with CF₃COOD) | m.p. 190–192° C. NMR (DMSO-d₆): 4.8(2H, s); 6.4(2H, s, exchangeable with CF₃COOD); 7.0(2H, m); 7.4 (2H, m); 7.7(1H, dd, J = 8.75 and 2Hz); 7.9(2H, m); 10.6(1H, s, exchangeable with CF₃COOD) |

EXAMPLE 28

2-Chloro-N-[3-chloro-4-nitromethylcarbonylphenyl]phenylacetamide a) Phenyl 2-chloro-4-[(2-chlorobenzyl)carbonylamino]benzoate 1.54 g (8 mmol) of 1-(3-dimethylaminopropyl)-3-ethylcarbodiimide hydrochloride are added to a suspension composed of 2 g (8 mmol) of the compound prepared in Example 12a, of 1.28 g (10.4 mmol) of 4-dimethylaminopyridine, and 80 ml of dichloromethane. The solution obtained is stirred for 15 min at room temperature, before adding 1.45 g (8.4 mmol) of 2-chlorophenylacetic acid in 20 ml of dichloromethane. The solution is stirred for 18 hours at room temperature. 200 ml of water and 20 ml of concentrated HCl are then added. The decanted organic phase is washed with a 1N HCl solution, and then with a sodium hydroxide solution, and with water until neutral, before being dried over Na₂SO₄ and concentrated. The residue is crystallized from 95° ethanol to give 1.4 g of white powder (Yield=43%).

m.p.=160–163° C.; NMR (DMSO-d₆): 3.95 (2H,s); 7.3–7.4 (5H,m); 7.5 (4H,m); 7.7 (1H,dd, J=8.7 Hz and 2.1 Hz); 8.05 (1H,d, J=2.1 Hz); 8.2 (1H,d, J=8.7 Hz); 10.8 (1H,s, exchangeable with CF₃COOD).

b) 2-Chloro-N-[3-chloro-4-nitromethylcarbonylphenyl]phenylacetamide

This compound was obtained by carrying out the procedure as in Example 1b.

m.p.=154–156° C.; NMR (DMSO-d₆): 3.95 (2H,s); 6.4 (2H,s exchangeable with CF₃COOD); 7.35 (2H,m); 7.45 (2H,m); 7.7 (1H,dd, J=8.7 Hz and 1.9 Hz); 7.95 (2H,m); 10.8 (1H,s, exchangeable with CF₃COOD).

EXAMPLES 29 AND 30

The compounds of Examples 29 and 30 were obtained by carrying out the procedure starting with the amine prepared in Example 12a as in Example 28.

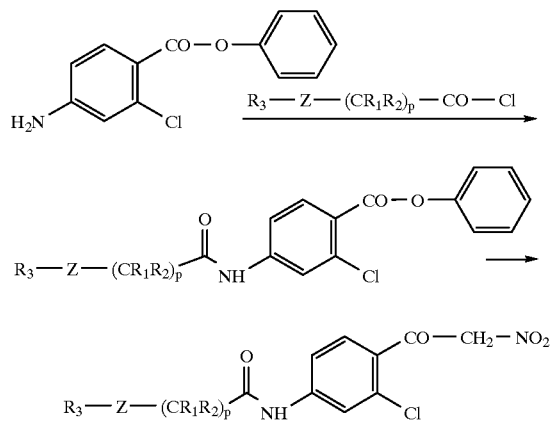

N-[3-Chloro-4-nitromethylcarbonylphenyl]-1-(4-chlorophenyl)cyclopropylcarboxamide (Example 29)
N-[3-Chloro-4-nitromethylcarbonylphenyl]-2-trifluoromethylphenylacetamide (Example 30)

| Examples | R3—Z—(CR₁R₂)ₚ | Phenyl esters | Compounds —CO—CH₂NO₃ |
|---|---|---|---|
| 29 | 1-(4-chlorophenyl)cyclopropyl structure | m.p. 119–121° C. NMR(DMSO-d₆): 1.25(2H, m); 1.6(2H, m); 7.3–7.55(9H, m); 7.8(1H, dd, J=8.7Hz and 2Hz); 8.0(1H, d, J=2Hz); 8.15(1H, d, J=8.7Hz); 9.7(1H, s, exchangeable with CF₃COOD) | m.p. 159–160° C. NMR(DMSO-d₆): 1.2(2H, m); 1.5(2H, m); 6.4(2H, s, exchangeable with CF₃COOD); 7.4(4H, s); 7.7 (1H, m); 7.9(2H, m); 9.6(1H, s, exchangeable with CF₃COOD) |

-continued

| Examples | R3—Z—(CR₁R₂)ₚ | Phenyl esters | Compounds —CO—CH₂NO₃ |
|---|---|---|---|
| 30 | 2-(CH₂-) and 6-(CF₃) substituted benzyl group | m.p. 160–162° C. NMR(DMSO-d₆): 4.05(2H, s); 7.35(3H, m); 7.5–7.8(7H, m); 8.05(1H, d, J=2Hz); 8.2(1H, d, J=8.7Hz); 10.8(1H, s, exchangeable with CF₃COOD) | m.p. 160–162° C. NMR(DMSO-d₆): 4.0(2H, s); 6.4(2H, s, exchangeable with CF₃COOD); 7.5–7.75(5H, m); 7.9(2H, m); 10.7(1H, s, exchangeable with CF₃COOD) |

EXAMPLE 31

N-[3-Chloro-4-nitromethylcarbonylphenyl]-4-chlorobenzenesulfonamide

A mixture composed of 2 g (9.3 mmol) of the amine obtained in Example 13, 1.5 ml (18.5 mmol) of pyridine, 2.95 g (13.9 mmol) of 4-chlorobenzenesulfonic acid chloride and 80 ml of THF is heated for 16 h at 40° C. After cooling, 100 ml of water and 5 ml of concentrated hydrochloric acid are added before extracting with ethyl acetate. The organic phase is washed with a dilute sodium hydroxide solution. This aqueous phase is then acidified with HCl and extracted with ethyl acetate, which is then washed with water until neutral, dried over $Na_2SO_4$ and concentrated under vacuum. The residue is purified by chromatography on a silica column in a dichloromethane/methanol (98:2) mixture. NMR (DMSO-d₆): 6.25 (2H, s, exchangeable with CF₃COOD); 7.0–7.3 (3H,m); 7.6–7.9 (4H,m); 11.2 (1H, broad s, exchangeable with CF₃COOD).

EXAMPLE 32

N-[3-Chloro-4-nitromethylcarbonylphenyl] benzenesulfonamide a) Phenyl-2-chloro-4-[phenylsulfonylamino]benzoate A mixture composed of 10 g (40.4 mmol) of the amine prepared in Example 12a, 6.5 ml (80.4 mmol) of pyridine, 10.7 g (60.5 mmol) of benzenesulfonic acid chloride and 200 ml of THF is stirred for 2 hours at room temperature, before being heated at 40° C. for 14 hours. After cooling, 200 ml of water and 5 ml of concentrated HCl are added. The reaction medium is extracted with dichloromethane, which is then washed with water until neutral, dried over $Na_2SO_4$ and concentrated under vacuum. The residue, purified by chromatography on a silica column with dichloromethane, gives 14.5 g of a light orange powder (Yield=92%).

m.p.=130–140° C.; NMR (DMSO-d₆): 7.2–7.4 (5H,m); 7.5 (2H,m); 7.65 (3H,m); 7.8 (2H,dd, J=7.5 Hz and 0.8 Hz); 8.1 (1H,d, J=7.5 Hz); 11.25 (1H,s, exchangeable with CF₃COOD).

b) N-[3-Chloro-4-nitromethylcarbonylphenyl] benzenesulfonamide

The compound was obtained by carrying out the procedure as in Example 1b.

NMR (DMSO-d₆): 6.4 (2H,s, exchangeable with CF₃COOD): 7.25 (2H,m); 7.7 (3H,m); 7.9 (3H,m); 11.2 (1H, broad s, exchangeable with CF₃COOD)

EXAMPLE 33

Nitromethyl 2-chloro-4-[N,N-di(phenylmethyl) amino]phenyl ketone a) Phenyl 2-chloro-4-[N,N-di(phenylmethyl)amino] benzoate A mixture of 2.5 g (10 mmol) of the amine prepared in Example 12a, 2.7 g (20 mmol) of potassium carbonate, 6.8 g (40 mmol) of benzyl bromide, a few crystals of potassium iodide and 100 ml of dimethylformamide is heated at 80° C. for 6 hours. After cooling, the reaction medium is poured into 300 ml of water, extracted with ethyl acetate, which is then washed with water, dried over $Na_2SO_4$ and concentrated. The residual oil is triturated in hexane and the solid obtained is recrystallized from ethanol, to give 1.6 g of an off-white solid (Yield=37%).

m.p.=133–135° C.; NMR (DMSO-d₆): 4.8 (4H,s); 6.7–6.85 (2H,m); 7.1–7.5 (15H,m); 7.9 (1H,m)

b) Nitromethyl 2-chloro-4-[N,N-di(phenylmethyl)-amino] phenyl ketone

This compound was obtained by carrying out the procedure as in Example 1b (Yield=40%).

m.p. 116–118° C.; NMR (DMSO-d₆): 4.9 (4H,s); 6.25 (2H, s, exchangeable with CF₃COOD); 6.8–6.9 (2H,m); 7.2–7.5 (10H,m); 7.7 (1H,d, J=9 Hz)

EXAMPLE 34

N-[2-Chloro-3-nitromethylcarbonylphenyl] acetamide a) Phenyl 3-amino-2-chlorobenzoate This compound was obtained from phenyl 2-chloro-3-nitrobenzoate by carrying out the procedure as in Example 12a (Yield=97%).

m.p.=46–48° C.; NMR (DMSO-d₆): 5.5 (2H,s, exchangeable with CF₃COOD); 6.85 (1H,dd, J=7.45 Hz and 2.3 Hz); 7.0 (2H,m); 7.1 (3H,m); 7.3 (2H,m)

b) Phenyl 3-acetylamino-2-chlorobenzoate

This compound was obtained by carrying out the procedure as in Example 12b (Yield=60%).

m.p.=120–122° C.; NMR (DMSO-d₆): 2.2 (3H, s); 7.4 (3H, m); 7.55 (3H, m); 7.9 (1H, m); 8.0 (1H, m); 9.8 (1H, s, exchangeable with CF₃COOD)

C) N-[2-Chloro-3-nitromethylcarbonylphenyl]acetamide

This compound was obtained by carrying out the procedure as in Example 1b.

m.p.=140–142° C.; NMR (DMSO-d₆): 2.2 (3H, s); 6.5 (2H, s, exchangeable with CF₃COOD); 7.6 (1H, m); 7.8 (1H, dd, J=8 Hz and 1.3 Hz); 8.1 (1H, dd, J=8 Hz and 1.3 Hz); 9.8 (1H, s, exchangeable with CF₃COOD)

EXAMPLE 35

N-[2-Chloro-3-nitromethylcarbonylphenyl]-2-methylphenylacetamide a) Phenyl 2-chloro-3-[(2-methylbenzyl)carbonylamino] benzoate This compound was obtained from phenyl 3-amino-2-chlorobenzoate and (2-methylphenyl)acetic acid chloride, the procedure being carried out as in Example 14a (Yield=78%).

m.p.=123–125° C.; NMR (CDCl₃): 2.3 (3H, s,); 3.75 (2H, s); 7.1–7.4 (10H, m); 7.65 (1H, m); 7.8 (1H, broad s, exchangeable with CF₃COOD); 8.6 (1H, dd, J=8.3 Hz and 1.55 Hz)

b) N-[2-Chloro-3-nitromethylcarbonylphenyl]-2-methylphenylacetamide

This compound was obtained by carrying out the procedure as in Example 1b (Yield=45%).

m.p.=130–132° C.; NMR (DMSO-d₆): 2.25 (3H, s); 3.8 (2H, s); 6.4 (2H, s, exchangeable with CF₃COOD); 7.1 (3H, m); 7.2 (1H, m); 7.45 (1H, m); 7.6 (1H, dd, J=7.75 Hz and 1.4 Hz); 7.9 (1H, dd, J=8.1 Hz and 1.3 Hz); 9.8 (1H, s, exchangeable with CF₃COOD)

EXAMPLE 36

N-[4-Chloro-3-nitromethylcarbonylphenyl] acetamide a) Phenyl 2-chloro-5-nitrobenzoate This compound was obtained from 2-chloro-5-nitrobenzoic acid, the procedure being carried out as in Example 1a (Yield=92%).

m.p.=83–85° C.; NMR (DMSO-$d_6$): 7.4 (3H, m); 7.55 (2H, m); 8.0 (1H, d, J=8.8 Hz); 8.5 (1H, dd, J=8.8 Hz and 2.7 Hz); 8.95 (1H, d, J=2.7 Hz)

b) Phenyl 5-amino-2-chlorobenzoate 18 g of Raney nickel are added to a solution of 59 g (212 mmol) of the compound prepared in step a) in 600 ml of dioxane. The mixture is hyrogenated at a pressure of 70 kg at 65° C. After filtration of the catalyst and concentration of the solvent, the residue is purified by chromatography on a silica column in dichloromethane and then in a dichloromethane/hexane (1:1) mixture to give 29.3 g of a yellow solid (Yield=55%).

m.p.=84–86° C.; NMR (CDCl$_3$): 3.8 (2H, broad s, exchangeable with CF$_3$COOD); 6.7 (1H, m); 7.2 (5H, m); 7.35 (2H, m)

c) Phenyl 5-acetylamino-2-chlorobenzoate

This compound was obtained from the amine prepared in step b), the procedure being carried out as in Example 12b (Yield=69%).

m.p.=141–143° C.; NMR (DMSO-$d_6$): 1.95 (3H, s); 7.2 (3H, m); 7.35 (2H, m) 7.5 (1H, d, J=8.7 Hz); 7.75 (1H, dd, J=8.7 Hz and 2.6 Hz); 8.25 (1H, d, J=2.6 Hz); 10.25 (1H, s, exchangeable with CF$_3$COOD)

d) N-[4-Chloro-3-nitromethylcarbonylphenyl]acetamide

The compound was obtained by carrying out the procedure as in Example 1b (Yield=15%).

m.p.=122–124° C.; NMR (DMSO-$d_6$): 2.2 (3H, s); 6.45 (2H, s exchangeable with CF$_3$COOD); 7.7 (1H, d, J=8.7 Hz); 7.9 (1H, dd, J=8.7 Hz and 2.5 Hz); 8.2 (1H, d, J=2.5 Hz); 10.5 (1H, s, exchangeable with CF$_3$COOD)

EXAMPLE 37

N-[4-Chloro-3-nitromethylcarbonylphenyl]-2-methylphenylacetamide a) Phenyl 2-chloro-5-[(2-methylbenzyl)carbonylamino]-benzoate This compound was obtained from the amine prepared in Example 36b, and (2-methylphenyl)acetic acid chloride, the procedure being carried out as in Example 14a (Yield=94%).

m.p.=102–104° C.; NMR (CDCl$_3$): 2.25 (3H, s); 3.75 (2H, s); 7.1–7.25 (9H, m, of which 1H is exchangeable with CF$_3$COOD); 7.35 (3H, m); 7.7 (1H, dd, J=8.7 Hz and 2.2 Hz); 7.85 (1H, d, J=2.2 Hz).

b) N-[4-Chloro-3-nitromethylcarbonylphenyl]-2-methylphenylacetamide

This compound was obtained by carrying out the procedure as in Example 1b (Yield=38%)

m.p.=148–150° C.; NMR (DMSO-$d_6$) 2.3 (3H, s); 3.8 (2H, s); 6.4 (2H, s, exchangeable with CF$_3$COOD); 7.2 (4H, m); 7.6 (1H, d, J=8.7 Hz); 7.8 (1H, dd, J=8.7 Hz and 2.5 Hz); 8.2 (1H, d, J=2.5 Hz); 10.6 (1H, s, exchangeable with CF$_3$COOD)

EXAMPLE 38

N-[4-Chloro-3-nitromethylcarbonylphenyl] benzenesulfonamide a) Phenyl 5-[benzenesulfonylamino]-2-chlorobenzoate This compound was obtained from the amine prepared in Example 36b by carrying out the procedure as in Example 32a (Yield=97%).

m.p.=about 50° C.; NMR (DMSO-$d_6$): 7.3–7.7 (10H, m); 7.8 (3H, m); 10.8 (1H, s, exchangeable with CF$_3$COOD)

b) N-[4-Chloro-3-nitromethylcarbonylphenyl] benzenesulfonamide

This compound was obtained by carrying out the procedure as in Example 1b.

m.p.=152–154° C.; NMR (DMSO-$d_6$): 6.2 (2H, s, exchangeable with CF$_3$COOD); 7.2 (1H, m); 7.35–7.65 (5H, m); 7.75 (2H, m); 10.8 (1H, s, exchangeable with CF$_3$COOD)

EXAMPLE 39

2-[(3-Chloro-4-nitromethylcarbonylphenyl) aminocarbonylmethylaminocarbonyl]benzoic acid a) Phenyl 2-chloro-4-((1,3-dihydro-1,3-dioxo-2H-isoindol-2-yl)methylcarbonylamino)benzoate This compound was obtained from the amine prepared in Example 12a, and (1,3-dihydro-1,3-dioxo-2H-isoindol-2-yl) acetic acid chloride (prepared from the corresponding acid and SOCl$_2$, m.p.=80–83° C.), the procedure being carried out as in Example 14a (Yield=54%).

m.p.=220–222° C.; NMR (DMSO-$_6$): 4.55 (2H, s); 7.25 (3H, m); 7.4 (2H, m); 7.6 (1H, m); 7.8–8.0 (5H, m); 8.1 (1H, d, J=8.6 Hz); 10.9 (1H, s, exchangeable with CF$_3$COOD)

b) 2-[(3-Chloro-4-nitromethylcarbonylphenyl) aminocarbonylmethylaminocarbonyl]benzoic acid 1.49 ml of nitromethane are added to a solution composed of 2.9 g (25.5 mmol) of potassium tert-butoxide and 50 ml of DMSO, maintained at a temperature below 20° C. The mixture is stirred for one hour at a temperature below 20° C. before adding, dropwise, 3.7 g (8.5 mmol) of the phenyl ester prepared in step a) dissolved in 90 ml of DMSO. After stirring for 16 hours at room temperature, the reaction medium is poured into 750 ml of water. This aqueous phase is washed with ethyl acetate and acidified with HCL. The precipitate formed is filtered, washed with water and dried under vacuum before being recrystallized from acetonitrile to give 2.2 g of a white powder (Yield=61%).

m.p.=206–209° C.; NMR (DMSO-$d_6$): 4.0 (2H, d, J=5.6 Hz, is converted to singlet with CF$_3$COOD); 6.3 (2H,s, exchangeable with CF$_3$COOD); 7.4–8.0 (7H, m); 8.75 (1H, t, J=s.6 Hz, exchangeable with CF$_3$COOD); 10.3 (1H, s, exchangeable with CF$_3$COOD); 13.1 (exchangeable with CF$_3$COOD)

EXAMPLE 40

N-[3-Chloro-4-nitromethylcarbonylphenyl]-(1,3-dihydro-1,3-dioxo-2H-isoindol-2-yl)acetamide HCl gas is bubbled for 1.5 hours through a suspension composed of 2 g (4.8 mmol) of the compound prepared in Example 39b and 30 ml of methanol. The heating of the solution allows the dissolution of the solid at around 60° C. After cooling, the precipitate formed is filtered and recrystallized from acetonitrile to give 0.4 g of an off-white powder (Yield=19%).

m.p.=121° C. (decomposition); NMR (DMSO-$d_6$): 4.5 (2H, s); 6.3 (2H, s, exchangeable with CF$_3$COOD); 7.55 (1H, dd, J=8.7 Hz and 2 Hz); 7.8–8.0 (6H, m); 10.9 (1H, s, exchangeable with CF$_3$COOD).

EXAMPLE 41

1-[3-[Chloro-4-nitromethylcarbonylphenyl]-3-(phenylsulfonyl)urea a) Phenyl 2-chloro-4-[phenylsulfonylaminocarbonylamino] benzoate 1.5 g (8.2 mmol) of phenylsulfonyl isocyanate in 20 ml of dichloromethane are added, dropwise, to a suspension of 2.08 g (8.4 mmol) of the amine prepared in Example 12a in 40 ml of dichloromethane. Complete solubilization is obtained upon addition of the first drops, followed by the formation of a thick precipitate. After stirring for 16 hours at room temperature, the precipitate is filtered and washed with dichloromethane and dried at 80° C. under vacuum to give 2.2 g of a white powder (Yield=62%).

m.p.=183–185° C.; NMR (DMSO-$d_6$): 7.0–7.9 (13H, m); 9.3 (1H, s, exchangeable with $CF_3COOD$); 11.0 (1H, s, exchangeable with $CF_3COOD$)

b) 1-[3-Chloro-4-nitromethylcarbonylphenyl]-3-(phenylsulfonyl)urea

This compound was obtained by carrying out the procedure as in Example 1b (Yield=49%).

m.p.=168–169° C.; NMR (DMSO-$d_6$): 6.35 (2H, s, exchangeable with $CF_3COOD$); 7.35 (1H, m); 7.5–7.7 (4H, m); 7.8 (1H, d, J=8.7 Hz); 8.0 (2H, m); 9.5 (1H, s, exchangeable with $CF_3COOD$); 11.3 (1H, broad s, exchangeable with $CF_3COOD$).

EXAMPLE 42

Nitromethyl 3-methyl-2-thienyl ketone

A solution composed of 10 g (70 mmol) of 3-methyl-2-thiophenecarboxylic acid, 3.4 g (56 mmol) of nitromethane and 115 ml of DMF is cooled to 0° C. 11.9 g (72.8 mmol) of diethyl cyanophosphonate in 56 ml of DMF, and then 18.2 g (180 mmol) of triethylamine in 56 ml of DMF are added thereto successively. The medium is then stirred for 2 hours at 0° C. and for 21 hours at room temperature. The reaction medium is poured over 1 litre of a toluene/ethyl acetate (1:1) mixture, and extracted with water. This aqueous phase, acidified with 40 ml of acetic acid, is extracted with a toluene/ethyl acetate (1:1) mixture. The organic extracts are washed with water and then with a saturated NaCl solution in water, before being dried over $Na_2SO_4$ and concentrated. The residue, purified by chromatography on a silica column in dichloromethane and then by recrystallization from an ethyl acetate-hexane mixture, gives 2 g of a pale yellow solid (Yield=19%).

m.p.=59–61° C.; NMR ($CDCl_3$): 2.6 (3H, s); 5.7 (2H, s, exchangeable with $CF_3COOD$); 7.1 (1H, d, J=4.9 Hz); 7.6 (1H, d, J=4.9 Hz).

EXAMPLE 43

N-[3-Chloro-4-nitromethylcarbonylphenyl]-2-methylphenylacetamide a) 2-Chloro-4-[(2-methylbenzyl)carbonylamino]benzoic acid 19.56 g (116 mmol) of (2-methylphneyl)acetic acid chloride are added, over 1 hour, to a mixture of 20 g (116 mmol) of 4-amino-2-chlorobenzoic acid, 12.9 g (127 mmol) of triethylamine and 150 ml of DMF dried over a molecular sieve. After stirring for 16 h at room temperature, the DMF is removed by evaporation under vacuum. The residue is washed with water and with dichloromethane to give, after drying, 19 g of an off-white powder (Yield=53%).

m.p.=214–218° C.; NMR (DMSO-$d_6$): 2.25 (3H, s); 3.8 (2H, s); 7.1–7.25 (4H, m); 7.55 (1H, dd, J=8.6 Hz and 2 Hz); 7.8 (1H, d, J=8.6 Hz); 7.9 (1H, d, J=2 Hz); 10.6 (1H, s, exchangeable with $CF_3COOD$); 13.1 (1H, broad s, exchangeable with $CF_3COOD$).

b) N-[3-Chloro-4-nitromethylcarbonylphenyl]-2-methylphenylacetamide

This compound was obtained by carrying out the procedure as in Example 42 starting with 19 g (62.5 mmol) of 2-chloro-4-[(2-methylbenzyl)carbonylamino]benzoic acid obtained in step a), 3.18 g of nitromethane, 11 g (67.6 mmol) of diethyl cyanophosphonate, 16.8 g (167 mmol) of triethylamine in 205 ml of DMF dried over a molecular sieve. After chromatography on a silica column (eluent: dichloromethanemethanol 95:5) and recrystallization from a hexane-ethyl acetate mixture, 0.2 g (Yield=1%) of a pale yellow powder is obtained.

m.p.=133–135° C.; NMR (DMSO-$d_6$): 2.3 (3H, s); 3.8 (2H, s); 6.45 (2H, s, exchangeable with $CF_3COOD$); 7.2–7.3 (4H, m); 7.75 (1H, dd, J=8.7 Hz and 2 Hz); 7.9 (2H, m); 10.8 (1H, s, exchangeable with $CF_3COOD$).

Removal of the washings makes it possible to isolate 5.2 g (Overall yield=30%) of a product identical to the first batch.

This compound is also obtained from the amine prepared in Example 12a by carrying out the procedure as in Example 28.

The phenyl ester intermediate (m.p.=120–123° C., yield=56%) is converted to the compound —CO—$CH_2$—$NO_2$ (m.p.=141–143° C. (acetonitrile)) with a yield of 43%.

EXAMPLE 44

N-[3-Chloro-4-nitromethylcarbonylphenyl]-2-oxopiperidine a) Phenyl 2-chloro-4-[5-chloropentanoylamino]benzoate This compound was obtained by carrying out the procedure as in Example 14a, starting with the compound prepared in Example 12a and 5-chloropentanoic acid chloride.

NMR (DMSO-$d_6$): 1.8 (4H, m); 2.5 (2H, t, J=6.7 Hz); 3.75 (2H, t, J=6.7 Hz); 7.3–7.6 (5H, m); 7.7 (1H, dd, J=8.7 Hz and 2 Hz); 8.1 (1H, d, J=2 Hz); 8.2 (1H, d, J=8.7 Hz); 10.5 (1H, s, exchangeable with $CF_3COOD$).

b) N-[3-Chloro-4-nitromethylcarbonylphenyl]-2-oxopiperidine

This compound was obtained by carrying out the procedure as in Example 1b (Yield=67%).

m.p.=119–120° C.; NMR (DMSO-$d_6$): 1.85 (4H, m); 2.45 (2H, t, J=6.3 Hz); 3.7 (2H, t, J=5.5 Hz); 6.4 (2H, s, exchangeable with $CF_3COOD$); 7.5 (1H, dd, J=8.5 Hz and 2 Hz); 7.7 (1H, d, J=2 Hz); 7.9 (1H, d, J=8.5 Hz)

EXAMPLES 45 and 46

The following are obtained starting with the amine prepared in Example 12a, the procedure being carried out as in Example 14:

N-[3-Chloro-4-nitromethylcarbonylphenyl]-1-(4-chlorophenyl)cyclopentanecarboxamide (Example 45)
N-[3-Chloro-4-nitromethylcarbonylphenyl]-2,3-dihydro-1H-indene-2-acetamide (Example 46)

| Examples | R₃—Z—(CR₁R₂)ₚ | Phenyl esters | Compounds —CO—CH₂NO₂ |
|---|---|---|---|
| 45 | (1-methylcyclopentyl-4-chlorophenyl group) | m.p. 118–120° C. NMR(DMSO-d₆): 1.6 1.7(4H, m); 2.0 (2H, m); 2.7 (2H, m); 7.3(3H, m); 7.5(6H, m); 7.8(1H, dd, J=9Hz and 2Hz); 8(1H, d, J=2Hz); 8.15(1H, d, J=9Hz); 9.7 (1H, s, exchangeable with CF₃COOD) | m.p=pasty solid NMR(DMSO-d₆): 1.6 (4H, m); 1.9(2H, m); 2.6(4H, m); 6.4 (2H, s, exchangeable with CF₃COOD); 7.4 (4H, s); 7.75(1H, dd, J=9Hz and 2Hz); 7.9(1H, d, J=9Hz); 7.95(1H, d, J=2Hz); 9.7(1H, s, exchangeble with CF₃COOD) |
| 46 | (indanyl-CH₂ group) | NMR(DMSO-d₆): 2.5(4H, m); 2.8 (1H, m); 3.1(2H, m); 7.6(1H, dd, J=9Hz and 2Hz); 8(1H, d, J=2Hz); 8.1(1H, d, J=9Hz); 10.5(1H, s, exchangeable with CF₃COOD) | m.p. 157–157.5° C. NMR(DMSO-d₆): 2.5 (4H, m); 2.8(1H, m); 3.1(2H, m); 6.3 (2H, s, exchangeable with CF₃COOD); 7.1 (4H, m); 7.6(1H, dd; J=9Hz and 2Hz); 7.8 (1H, d, J=9Hz); 7.9 (1H, d, J=2Hz); 10.4(1H, s, exchangeable with CF₃COOD) |

EXAMPLES 47 to 57

The following are obtained starting with the amine prepared in Example 12a, the procedure being carried out as in Example 28:

N-[3-Chloro-4-nitromethylcarbonylphenyl]-4-chlorobenzeneacetamide (Example 47)

N-[3-Chloro-4-nitromethylcarbonylphenyl]-3-chlorobenzeneacetamide (Example 48)

N-[3-Chloro-4-nitromethylcarbonylphenyl]-3,4-dichlorobenzeneacetamide (Example 49)

N-[3-Chloro-4-nitromethylcarbonylphenyl]-4-methylbenzeneacetamide (Example 50)

N-[3-Chloro-4-nitromethylcarbonylphenyl]-3-methylbenzeneacetamide (Example 51)

N-[3-Chloro-4-nitromethylcarbonylphenyl]-3,4-dimethylbenzeneacetamide (Example 52)

N-[3-Chloro-4-nitromethylcarbonylphenyl]-4-trifluoromethylbenzeneacetamide (Example 53)

N-[3-Chloro-4-nitromethylcarbonylphenyl]-4-methoxybenzeneacetamide (Example 54)

N-[3-Chloro-4-nitromethylcarbonylphenyl]-4-nitrobenzeneacetamide (Example 55)

4-Bromo-N-[3-chloro-4-nitromethylcarbonylphenyl]-2-fluorobenzeneacetamide (Example 56)

N-[3-Chloro-4-nitromethylcarbonylphenyl]-4-fluorobenzeneacetamide (Example 57)

| Examples | R₃—Z—(CR₁R₂)ₚ | Phenyl esters | Compounds —CO—CH₂NO₂ |
|---|---|---|---|
| 47 | (4-chlorobenzyl, H₂C—) | m.p. 140–142° C. NMR (DMSO-d₆): 3.8 (2H, s); 7.4(9H, m); 7.7(1H, dd, J = 9Hz and 2Hz); 8.0 (1H, d, J = 2Hz); 8.2(1H, d, J = 9Hz); 10.8(1H, s, exchangeable with CF₃COOD) | m.p. 158–160° C. NMR (DMSO-d₆): 3.6 (2H, s); 6.3(2H, s, exchangeable with CF₃COOD); 7.4(4H, m); 7.6(1H, dd, J = 9Hz and 2Hz); 7.9 (2H, m); 10.7(1H, s, exchangeable with CF₃COOD) |
| 48 | (3-chlorobenzyl, H₂C—) | m.p. 112–114° C. NMR (DMSO-d₆): 3.8 (2H, s); 7.4(9H, m); 7.75(1H, dd, J = 9Hz and 2Hz); 8.0 (1H, d, J = 2Hz); 8.2(1H, d, J = 9Hz); 10.8(1H, s, exchangeable with CF₃COOD) | m.p. 131–134° C. NMR (DMSO-d₆): 3.7 (2H, s); 6.35(2H, s, exchangeable with CF₃COOD); 7.3(4H, m); 7.6(1H, dd, J = 9Hz and 2Hz); 7.9 (2H, m); 10.7(1H, s, exchangeable with CF₃COOD) |
| 49 | (3,4-dichlorobenzyl, H₂C—) | m.p. 155–158° C. NMR (DMSO-d₆): 3.8 (2H, s); 7.2–7.7 (9H, m); 8.0(1H, d, J = 2Hz); 8.2(1H, d, J = 9Hz); 10.8 (1H, s, exchangeable with CF₃COOD) | m.p. = 160–162° C. NMR (DMSO-d₆): 3.7 (2H, s); 6.4(2H, s, exchangeable with CF₃COOD); 7.3(1H, dd, J = 8Hz and 2Hz); 7.6(3H. m); 7.9 (2H, m); 10.7(1H, s, exchangeable with CF₃COOD) |

-continued

| Examples | R₃—Z—(CR₁R₂)ₚ | Phenyl esters | Compounds —CO—CH₂NO₂ |
|---|---|---|---|
| 50 | 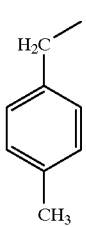 | m.p. = 130–132° C. NMR (DMSO-d₆): 2.0 (3H, s); 3.4(2H, s); 7.1(7H, m); 7.3 (2H, m); 7.4(1H, dd, J = 9Hz and 2Hz); 7.8(1H, d, J = 2Hz); 7.95(1H, d, J = 9Hz); 10.4(1H, s, exchangeable with CF₃COOD) | m.p. = 132–133° C. NMR (DMSO-d₆): 2.3 (3H, s); 3.6(2H, s); 6.3(2H, s, exchangeable with CF₃COOD); 7.15(4H, m); 7.6 (1H, dd, J = 9Hz); 7.9(2H, m); 10.6 (1H, s, exchangeable with CF₃COOD) |
| 51 | 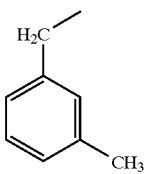 | m.p. = 126–128° C. NMR (DMSO-d₆): 2.3 (3H, s); 3.7(2H, s); 7.2(7H, m); 7.5 (2H, m); 7.7(1H, dd, J = 9Hz and 2Hz); 8.1(1H, d, J = 2Hz); 8.2(1H, d, J = 9Hz); 10.8(1H, s, exchangeable with CF₃COOD) | m.p. = 115–117° C. NMR (DMSO-d₆): 2.2 (3H, s); 3.5(2H, s); 6.3(2H, s, exchangeable with CF₃COOD); 7.0(4H, m); 7.55 (1H, dd, J = 7.6Hz and 1.7Hz); 7.8 (2H, m); 10.7(1H, s, exchangeable with CF₃COOD) |
| 52 | 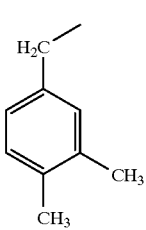 | m.p. = 156–158° C. NMR (DMSO-d₆): 2.2 (6H, 2s); 3.7 (2H, s); 7.1(3H, m); 7.3(3H, m); 7.5 (2H, m); 7.7(1H, dd, J = 9Hz and 2Hz); 8(1H, d, J = 2Hz); 8.15(1H, d, J = 9Hz); 10.8(1H, s, exchangeable with CF₃COOD) | m.p. = 128–129° C. NMR (DMSO-d₆): 2.1 (6H, 2s); 3.5(2H, s); 6.25(2H, s, exchangeable with CF₃COOD); 7.0(3H, m); 7.5 (1H, dd, J = 9Hz and 2Hz); 7.85(2H, m); 10.7(1H, s, exchangeable with CF₃COOD) |
| 53 | 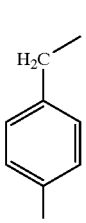 | m.p. = 135–137° C. NMR (DMSO-d₆): 3.9 (2H, s); 7.3–7.8 (10H, m); 8.0 (1H, d, J = 2Hz); 8.15(1H, d, J = 9Hz); 10.8(1H, s, exchangeable wit CF₃COOD) | m.p. = 164–165° C. NMR (DMSO-d₆): 3.8 (2H, s); 6.4(2H, s, exchangeable with CF₃COOD); 7.6(5H, m); 7.9(2H, m); 10.8 (1H, s, exchangeable with CF₃COOD) |
| 54 | 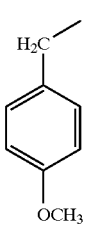 | m.p. = 147–149° C. NMR (DMSO-d₆): 3.6 (2H, s); 3.8(3H, s); 6.9(2H, s); 7.3 (5H, m); 7.5(2H, m); 7.7(1H, dd, J = 8Hz and 2Hz); 8.0 (1H, d, J = 2Hz); 8.15(1H, d, J = 8Hz); 10.7(1H, s, exchangeable with CF₃COOD) | m.p. 147–149° C. NMR (DMSO-d₆): 3.75 (2H, s); 3.8(3H, s); 6.5(2H, s, exchangeable with CF₃COOD); 7.0(2H, m); 7.4 (2H, m); 7.7(1H, dd, J = 9Hz and 2Hz); 8.1 (2H, m); 10.8(1H, s, exchangeable with CF₃COOD) |
| 55 | 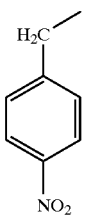 | m.p. 180–182° C. NMR (DMSO-d₆): 4.0 (2h, s); 7.4(3H, m); 7.5(2H, m); 7.7 (3H, m); 8.0(1H, d, J = 2Hz);8.15 (1H, J = 8.5Hz); 8.25(2H, m); 10.8 (1H, s, exchangeable with CF₃COOD) | m.p. 192–193° C. NMR (DMSO-d₆): 3.9 (2H, s); 6.3(2H, s, exchangeable with CF₃COOD); 7.6(3H, m); 7.8(2H, m); 8.2 (2H, m); 10.8(1H, s, exchangeable with CF₃COOD) |

| Examples | $R_3$—Z—$(CR_1R_2)_p$ | Phenyl esters | Compounds —CO—$CH_2NO_2$ |
|---|---|---|---|
| 56 | 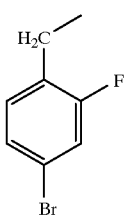 | m.p. = 173–175° C. NMR (DMSO-$d_6$): 3.9 (2H, s); 7.5(8H, m); 7.7(1H, dd, J = 8.6hz and 1.9Hz); 8.1(1H, d, J = 1.9Hz); 8.2(1H, d, J = 8.6Hz); 10.8 (1H, s, exchangeable with $CF_3COOD$) | m.p. 165–167° C. NMR (DMSO-$d_6$): 3.8 (2H, s); 6.25(2H, s, exchangeable with $CF_3COOD$); 7.3(2H, m); 7.55(2H, m); 10.7(1H, s, exchangeable with $CF_3COOD$) |
| 57 | 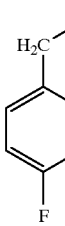 | m.p. 132–134° C. NMR (DMSO-$d_6$): 3.75 (2H, s); 7.4(9H, m); 7.7(1H, dd, J = 9Hz and 2Hz); 8.0 (1H, d, J = 2Hz); 8.15(1H, d, J = 9Hz); 10.7(1H, s, exchangeable with $CF_3COOD$) | m.p. 139–141° C. NMR (DMSO-$d_6$): 3.8 (2H, s); 6.5(2H, s, exchangeable with $CF_3COOD$): 7.3(2H, m); 7.5(2H, m); 7.75 (1H, dd, J = 9Hz and 2Hz); 8.0(2H, m); 10.8(1H, s, exchangeable with $CF_3COOD$) |

EXAMPLE 58

N-[3-Chloro-4-nitromethylcarbonylphenyl]-2-propeneamide

Obtained by carrying out the procedure as in Example 31, starting with the amine prepared in Example 13, in the presence of triethylamine and in dichloromethane.

m.p. 140–144° C.; NMR (DMSO-$d_6$): 6.35 (2H, s, exchangeable with $CF_3COOD$); 6.8 (1H, d, J=12 Hz); 7.4 (3H, m); 7.65 (4H, m); 7.9 (1H, d, J=9 Hz); 8.1 (1H, d, J=2 Hz); 10.8 (1H, s, exchangeable with $CF_3COOD$).

EXAMPLE 59

N-[3-Methyl-4-nitromethylcarbonylphenyl]-2-methylphenylacetamide a) Phenyl 2-methyl-4-nitrobenzoate Obtained by carrying out the procedure as in Example 1a, starting with 2-methyl-4-nitrobenzoic acid.

b) Phenyl 4-amino-2-methylbenzoate

A mixture composed of 3.5 g (13.6 mmol) of the nitro derivative prepared in Example 59a, 1 g of Raney nickel and 35 ml of dioxane is subjected to a hydrogen pressure of about 100 atm, for 2.5 h at 80° C. After cooling, filtration of the reaction medium, and concentration, 2.7 g of a pasty solid are obtained.

NMR (DMSO-$d_6$): 2.5 (3H, s); 6.1 (2H, s, exchangeable with $CF_3COOD$); 6.5 (2H, m); 7.2 (3H, m); 7.4 (2H, m); 7.8 (1H, d, J=8.3 Hz)

c) Phenyl 2-methyl-N-[(2-methylphenyl)carbonylamino]benzoate

Obtained by carrying out the procedure as in Example 14a, starting with the amine prepared in Example 59b and (2-methyl)phenylacetic acid chloride (Yield=86%).

NMR (DMSO-$d_6$): 2.3 (3H, s); 2.6 (3H, s); 3.7 (2H, s); 7.1–7.7 (11H, m); 8.1 (1H, d, J=9 Hz); 10.5 (1H, s, exchangeable with $CF_3COOD$).

d) N-[3-Methyl-4-nitromethylcarbonylphenyl]-2-methylphenylacetamide

Obtained by carrying out the procedure as in Example 1b, starting with the phenyl ester prepared in Example 59c.

m.p. 159–160° C.; NMR (DMSO-$_6$): 2.1 (3H, s); 2.25 (3H, s); 3.5 (2H, s); 6.15 (2H, s, exchangeable with $CF_3COOD$); 7.0 (4H, m); 7.3 (1H, d, J=1.6 Hz); 7.45 (1H, dd, J=8.5 Hz and 1.6 Hz); 7.6 (1H, d, J=8.5 Hz); 10.4 (1H, s, exchangeable with $CF_3COOD$)

EXAMPLE 60

N-[2-Bromo-4-nitromethylcarbonylphenyl]-2-methylphenylacetamide a) 3-Bromo-4-([2-methylphenyl)carbonylamino]benzoic acid Obtained by carrying out the procedure as in Example 43a, starting with 4-amino-3-bromobenzoic acid and 2-methylphenylacetic acid chloride (Yield=86%).

NMR (DMSO-$d_6$): 2.1 (3H, s); 3.6 (2H, s); 6.9 (3H, m) 7.0 (1H, m); 7.75 (1H, m); 7.9 (1H, d, J=1.3 Hz); 9.3 (1H, s, exchangeable with $CF_3COOD$); 13.0 (1H, broad s, exchangeable with $CF_3COOD$)

b) Phenyl 3-bromo-4-[(2-methylphenyl)carbonylamino]benzoate

Obtained by carrying out the procedure as in Example 1a (Yield=98%)

m.p. 139–141° C.; NMR (DMSO-$d_6$): 2.4 (3H, s); 3.9 (2H, s); 7.2–7.5 (9H, m); 8.1 (2H, m); 8.3 (1H, d, J=1.8 Hz); 9.7 (1H, s, exchangeable with $CF_3COOD$).

c) N-[2-Bromo-4-nitromethylcarbonylphenyl]-2-methylphenylacetamide

Obtained by carrying out the procedure as in Example 1b (Yield=41%)

m.p. 125–127° C.; NMR (DMSO-$d_6$): 2.2 (3H, s); 3.7 (2H, s); 6.3 (2H, s, exchangeable with $CF_3COOD$); 7.1 (4H, m); 7.8 (1H, dd, J=9 Hz and 2 Hz); 7.9 (1H, m); 8.1 (1H, d, J=2 Hz); 9.5 (1H, s, exchangeable with $CF_3COOD$).

EXAMPLE 61

Nitromethyl 2-chloro-4-methoxyphenyl ketone a) Phenyl 2-chloro-4-methoxybenzoate Obtained by carrying out the procedure as in Example 1a, starting with 2-chloro-4-methoxybenzoic acid (Yield=770%)

NMR ($CDCl_3$): 3.8 (3H, s); 6.8 (1H, dd, J=9 Hz and 2.5 Hz); 6.95 (1H, d, J=2.5 Hz); 7.15 (3H, n); 7.3 (2H, m); 8.0 (1H, d, J=9 Hz)

b) Nitromethyl 2-chloro-4-methoxyphenyl ketone

Obtained by carrying out the procedure as in Example 1b.
NMR (DMSO-$d_6$): 3.9 (3H, s); 6.4 (2H, s, exchangeable with $CF_3COOD$); 7.1 (1H, dd, J=9 Hz and 2.5 Hz); 7.2 (1H, d, J=2.5 Hz); 7.9 (1H, d, J=9 Hz)

EXAMPLE 62

Nitromethyl 2-isopropylphenyl ketone
a) Phenyl 2-isopropylbenzoate
Obtained by carrying out the procedure as in Example 1a, starting with 2-(1-methylethyl)benzoic acid (Yield=85%).
NMR ($CDCl_3$): 1.2 (6H, m); 3.8 (1H, m); 7.1–7.25 (4H, m); 7.3–7.5 (4H, m); 7.9 (1H, dd, J=8 Hz and 1.5 Hz)
b) Nitromethyl 2-isopropylphenyl ketone
Obtained by carrying out the procedure as in Example 1b (Liquid)
NMR ($CDCl_3$): 1.5 (6H, m); 3.4 (1H, m); 5.7 (1H, s, exchangeable with $CF_3COOD$); 7.2–7.5 (4H, m)

EXAMPLE 63

N-[4-Chloro-3-nitromethylcarbonylphenyl]-2-mnethylphenylacetamide
a) 5-Chloro-2-[(2-methylphenyl) carbonylamino]benzoic acid
Obtained by carrying out the procedure as in Example 43a, starting with 2-amino-5-chlorobenzoic acid and 2-methylphenylacetic acid chloride (Yield=75%)
m.p.=224–226° C. NMR (DMSO-$d_6$): 2.3 (3H, s); 3.8 (2H, s); 7.2 (4H, m); 7.7 (1H, dd, J=9 Hz and 2.5 Hz); 7.9 (1H, d, J=2.5 Hz); 8.7 (1H, d, J=9 Hz); 11.1 (1H, s, exchangeable with $CF_3COOD$); 14.0 (1H, broad s, exchangeable with $CF_3COOD$)
b) Phenyl 5-chloro-2-[(2-methylphenyl)carbonylamino] benzoate
Obtained by carrying out the procedure as in Example 1a (Yield=38%)
c) N-[4-Chloro-2-nitromethylcarbonylphenyl-2-methylphenylacetamide
Obtained by carrying out the procedure as in Example 1b.
m.p.=128–130° C.; NMR (DMSO-$d_6$): 2.4 (3H, s); 3.9 (2H, s); 6.5 (2H, s, exchangeable with $CF_3COOD$); 7.4 (4H, m); 7.9 (1H, dd, J=9 Hz and 2 Hz); 8.1 (1H, d, J=2 Hz); 8.3 (1H, d, J=9 Hz); 10.9 (1H, s, exchangeable with $CF_3COOD$)

EXAMPLE 64

Nitromethyl 2-chloro-4-phenylthiophenyl ketone
a) Phenyl 2-chloro-4-(phenylthio)benzoate
A solution of 4.15 g (60.5 mmol) of sodium nitrite in 20 ml of water is added, at 0° C., to a suspension of 15 g (60.5 mmol) of the amine prepared in Example 12a, in 12.1 ml of 10N hydrochloric acid.
After stirring for one hour at 0° C., the medium is neutralized with a saturated sodium acetate solution. This mixture is poured, over 15 minutes, over a solution, at 70–80° C., composed of 8 g (72.6 mmol) of thiophenol, 3.85 g (96 mmol) of sodium hydroxide and 25 ml of water. At the end of the addition, the reaction medium is heated for 1 hour at 95° C. After cooling, the reaction medium is extracted with ethyl acetate. The organic phase, after washing with a dilute sodium hydroxide solution and then with water, is dried over $Na_2SO_4$ and concentrated under vacuum. The residue is purified by flash chromatography on silica (hexane) to give an orange-yellow liquid (Yield=31%).
NMR (DMSO-$_6$): 7.3–7.7 (12H, m); 8.1 (1H, m).
b) Nitromethyl 2-chloro-4-phenylthiophenyl ketone
Obtained by carrying out the procedure as in Example 1b.

m.p.=77–78° C.; NMR (DMSO-$_6$): 6.5 (2H, s); 7.3 (2H, m); 7.7 (5H, m); 7.95 (1H, d, J=8.5 Hz)

EXAMPLE 65

N-[3-Chloro-4-nitromethylcarbonylphenyl]-4-[(3-chloro-4-nitromethylcarbonylphenyl) aminocarbonyl]-3-phenylbutanamide
a) Phenyl 2-chloro-4-[[[[3-chloro-4-(Phenoxycarbonyl) phenyl]amino]-1,5-dioxo-3-phenylpentyl]amino]benzoate
Obtained by carrying out the procedure as in Example 14, starting with the amine prepared in Example 12a and a ½ equivalent of 3-phenylglutaric acid dichloride.
NMR (DMSO-$d_6$): 2.8 (4H, m); 3.8 (1H, m); 7.1–7.6 (17H, m); 7.9 (2H, d, J=2 Hz); 8.1 (2H, d, J=9 Hz); 10.4 (2H, s, exchangeable with $CF_3COOD$).
b) N-[3-Chloro-4-nitromethylcarbonylphenyl]-4-[(3-chloro-4-nitromethylcarbonylphenyl)aminocarbonyl]-3-phenylbutanamide
Obtained by carrying out the procedure as in Example 1b.
m.p. 195–196° C.; NMR (DMSO-$d_6$): 2.8 (4H, m); 3.8 (1H, m); 6.4 (4H, s, exchangeable with $CF_3COOD$); 7.3 (5H, m); 7.5 (2H, dd, J=9 Hz and 2 Hz); 7.9 (4H, m); 10.5 (s, exchangeable with $CF_3COOD$).

EXAMPLE 66

Nitromethyl 2-chloro-4-phenylsulfinylphenyl ketone
a) Phenyl 2-chloro-4-(phenylsulfinyl)benzoate
5 ml (40 mmol) of a 70% tert-butyl hydroperoxide solution in water are added to a suspension of 2 g (5.9 mmol) of the compound prepared in Example 64a in 60 ml of water. The reaction medium is heated at 70° for 32 h. After cooling, the peroxides are destroyed by addition of a solution of 10 g of sodium metabisulfite in 100 ml of water. After stirring for 2 hours and negative control for the peroxides, the reaction medium is extracted with dichloromethane. The organic phase is washed with a saturated NaCl solution in water and dried over $Na_2SO_4$. After concentration of the dichloromethane and purification by flash chromatography on a silica column (hexane-ethyl acetate 4:1), 0.1 g of a colourless oil is obtained (Yield=4%).
NMR (DMSO-$d_6$): 7.1 (3H, m); 7.2–7.4 (5H, m); 7.7 (3H, m); 7.8 (1H, d, J=1.6 Hz); 8.0 (1H, m)
b) Nitromethyl 2-chloro-4-phenylsulfinyl ketone
Obtained by carrying out the procedure as in Example 1b. (Oil).
NMR (DMSO-$d_6$): 6.4 (2H, s, exchangeable with $CF_3COOD$); 6.8 (3H, m); 7.2 (2H, m); 7.6 (3H, m)

EXAMPLE 67

Nitromethyl 4-chloro-2-trifluoromethoxyphenyl) ketone
a) Phenyl 4-chloro-2-trifluoromethoxybenzoate
In a hermetically closed steel container, a mixture composed of 21.5 g (112 mmol) of 4-chloro-2-hydroxybenzoic acid chloride, 59.8 g (336 mmol) of antimony trifluoride, 3.2 g of antimony pentafluoride and 258 ml of $CCl_4$, is heated at 175° C. for 6 h. After cooling, the reaction medium is taken up in about 3 l of dichloromethane. The organic phase is washed with water. The precipitate formed is washed with dichloromethane. The combined organic phases are dried over $Na_2SO_4$ and concentrated to give 19.2 g of a black liquid which is used without further purification.
The 19.2 g of the compound obtained above are mixed with 90 ml of toluene, 75 ml of thionyl chloride and a few drops of DMF, are stirred for 2 h at room temperature. The reaction medium is then concentrated under vacuum. The residue obtained is diluted with 200 ml of dichloromethane before being added to a mixture of 9.8 g of phenol, 16.2 g of triethylamine and 100 ml of dichloromethane. After stirring for 16 h at room temperature, the reaction medium is poured over an ice+HCL mixture. The mixture is extracted with dichloromethane, which is then washed with a dilute sodium hydroxide solution, and with water before being dried over $Na_2SO_4$, and concentrated. The residue is purified with chromatography on silica (hexane-ethyl acetate 4:1) to give 9.2 g of an orange-coloured liquid (Yield=37%).

b) Nitromethyl 4-chloro-2-trifluoromethoxyphenyl ketone

Obtained by carrying out the procedure as in Example 1b. Pasty solid

NMR ($CDCl_3$): 5.7 (2H, s, exchangeable with $CF_3COOD$); 7.3–7.5 (2H, m); 8.0 (1H, d, J=9 Hz).

EXAMPLE 68

N-[2-(3-Chloro-4-nitromethylcarbonylphenyl]-2-methylbenzenesulfonamide a) Ethyl 2-chloro-4-(cyanomethyl)benzoate 3.1 g (11.2 mmol) of ethyl 4-(bromomethyl)-2-chlorobenzoate are added dropwise to a solution composed of 0.94 g (14.3 mmol) of potassium cyanide, 3.75 ml of water and 8.8 ml of ethanol, heated under reflux. After refluxing for 3 hours, the medium is poured over 200 ml of water, and extracted with ethyl acetate. The organic phase is washed with a dilute HCl solution and then with water saturated with NaCl. The oil obtained after concentration of the organic phase is purified by flash chromatography on silica (hexane-ethyl acetate 1:0 to 1:1 gradient). 0.4 g of a brown solid is obtained (Yield=16%).

m.p. 60° C.; NMR ($CDCl_3$): 1.4 (3H, t, J=7 Hz); 3.8 (2H, s); 4.5 (2H, q, J=7 Hz); 7.1 (1H, m); 7.5 (1H, d); 7.9 (1H, d)

b) Ethyl 4-(2-aminoethyl)-2-chlorobenzoate

A mixture composed of 1.9 g (8.5 mmol) of ethyl 2-chloro-4-(cyanomethyl)benzoate, 0.5 g of Raney nickel in 70 ml of methanol containing a few ml of liquid ammonia is subjected to a hydrogen pressure of about 60 kg/cm², at 50° C. for 5 h, and then at 80° C. for 4.5 h. After filtration of the reaction medium, 1.5 g of oil are obtained (Yield=77%).

NMR ($CDCl_3$): 1.3 (3H, t, J=7 Hz); 1.7 (2H, broad s, exchangeable with $CF_3COOD$); 2.6–3.0 (4H, m); 4.3 (2H, q, J=7 Hz); 7.0 (1H, m); 7.2 (1H, m); 7.6 (1H, d, J=6.3 Hz)

c) Ethyl 2-chloro-4-[2-(2-methylphenylsulfonylamino) ethyl]benzoate

Obtained by carrying out the procedure as in Example 32c (Yield=43%).

(Oil).

NMR ($CDCL_3$): 1.3 (3H, t, J=7 Hz); 2.4 (3H, s); 2.7 (2H, m); 3.1 (2H, m); 4.3 (2H, q, J=7 Hz); 4.4 (1H, broad s, exchangeable with $CF_3COOD$); 6.9 (1H, m); 7.0 (1H, m); 7.1–7.4 (3H, m); 7.7 (1H, m); 7.8 (1H, dd, J=8 Hz and 1.25 Hz)

d) 2-Chloro-4-[2-(2-methylphenylsulfonylamino) ethylbenzoic acid

A mixture composed of 1 g (2.6 mmol) of the ethyl ester previously prepared, 18 ml of methanol, 18 ml of water and 0.2 g (5.2 mmol) of NaOH pellets, is heated for 4 h at 40° C. After concentration of the methanol and addition of 30 ml of water, the medium is washed with $CH_2Cl_2$. The aqueous phase is then acidified to give 0.675 g of a white precipitate (Yield=72%).

m.p. 122–124° C.; NMR (DMSO-$d_6$): 2.3 (3H, s); 2.7 (2H, m); 3.0 (2H, m); 7.0–7.8 (8H, m, of which 1H is exchangeable with $CF_3COOD$); 13.1 (1H, broad s, exchangeable with $CF_3COOD$)

e) Phenyl 2-chloro-4-[2-(2-methylphenylsulfonylamino) ethyl]benzoate

Obtained by carrying out the procedure as in 1a as the whole (Yield=61%).

(Oil).

NMR ($CDCl_3$): 2.4 (3H, s); 2.7 (2H, m); 3.2 (2H, m); 4.1 (1H, m, exchangeable with $D_2O$); 7.0–8.0 (12H, m)

f) N-[2-(3-Chloro-4-nitromethylcarbonylphenyl)ethyl]-2-methylbenzenesulfonamide

Obtained by carrying out the procedure as in Example 1b. (Oil).

NMR ($CDCl_3$): 2.5 (3H, s); 2.7 (2H, t, J=5 Hz); 3.2 (2H, t, J=5 Hz); 4.4 (1H, broad s, exchangeable with $CF_3COOD$); 5.8 (2H, s, exchangeable with $CF_3COOD$); 7.0–7.5 (5H, m); 7.6 (1H, m); 7.9 (1H, m)

EXAMPLE 69

N-[3-Bromo-4-nitromethylcarbonylphenyl]-2-methylphenylacetamide a) 2-Bromo-4-[(2-methylbenzyl)carbonylamino]benzoic acid Obtained by carrying out the procedure as in Example 43, starting with 4-amino-2-bromobenzoic acid (Yield=23%).

m.p.=decomposition at 205° C.; NMR (DMCO-$d_6$): 2.4 (3H, s); 3.9 (2H, s); 7.2 (4H, m); 7.6 (1H, dd, J=9 Hz and 2 Hz); 7.9 (1H, d, J=9 Hz); 8.2 (1H, d, J=2 Hz); 10.7 (1H, s, exchangeable with $CF_3COOD$); 13.0 (1H, broad s, exchangeable with $CF_3COOD$)

b) Phenyl 2-bromo-4-[(2-methylbenzyl)carbonylamino] benzoate

Obtain by carrying out the procedure as in Example 14a (Yield=quantitative)

(Oil).

NMR (DMSO-$d_6$): 2.0 (3H, s); 3.7 (2H, s); 6.8–7.3 (9H, m); 7.5 (1H, dd, J=8 Hz and 2 Hz); 7.8 (1H, d, J=8 Hz); 8.0 (1H, d, J=2 Hz); 10.5 (1H, s, exchangeable with $CF_3COOD$)

c) Phenyl 2-bromo-4-[(2-methylbenzyl)carbonylamino] benzoate

Obtained by carrying out the procedure as in Example 1b (Oil).

NMR (DMSO-$d_6$): 2.4 (3H, s); 3.8 (2H, s); 6.5 (2H, s, exchangeable with $CF_3COOD$); 7.2–7.6 (4H, m); 7.8 (1H, dd, J=9 Hz and 2 Hz); 8.0 (1H, d, J=9 Hz); 8.3 (1H, d, J=2 Hz); 10.9 (1H, s, exchangeable with $CF_3COOD$)

EXAMPLE 70

N-[3-Chloro-4-nitromethylcarbonylphenyl]-N-isopropylbenzenesulfonamide a) Phenyl 2-chloro-4-[(isopropyl)(phenylsulfonyl)amino] benzoate 10.1 g (25.5 mmol) of sodium hydride (at 55% in oil) are added to a solution of 9.9 g (25.5 mmol) of the compound prepared in Example 32a, in 100 ml of DMF. After stirring for 1 hour at room temperature, 9.4 g (76.5 mmol) of 2-bromopropane are added and the medium is stirred at room temperature for 16 hours before heating at 60° C. for 34 hours. 5.1 ml (51 mmol) of 2-iodopropane are then added. The reaction medium is then heated for 4 hours at 60° C. before being poured over a water-ice-HCl mixture. The medium is extracted with ethyl acetate, which is then dried and concentrated to give an oil. After purification by chromatography on a silica column ($CH_2Cl_2$) 1.9 g of off-white crystals are obtained (Yield=17%).

m.p. 120° C.; NMR (DMSO-$d_6$): 1.0 (6H, d, J=6.5 Hz); 4.4 (1H, m); 7.1–7.9 (12H, m); 8.0 (1H, d, J=8 Hz)

b) N-[3-Chloro-4-nitromethylcarbonylphenyl]-N-isopropylbenzenesulfonamide

Obtained by carrying out the procedure as in Example 1b, starting with the phenyl ester prepared in Example 65a.

(Oil)

NMR (CDCl$_3$): 1.0 (6H, d, J=7 Hz); 4.5 (1H, q, J=7 Hz); 5.8 (2H, s, exchangeable with CF$_3$COOD); 7.0 (1H, dd, J=9 Hz and 2 Hz); 7.15 (1H, m); 7.35–7.7 (6H, m).

What is claimed is:

1. A compound of the formula:

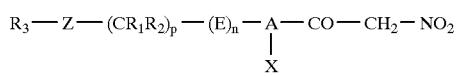

(I)

in which

A represents C$_6$–C$_{10}$-aryl;

X represents halogen, cyano, C$_1$–C$_7$-alkyl, trifluoromethyl, C$_3$–C$_7$ alkoxy or trifluoromethoxy;

R$_1$ and R$_2$, which are identical or different, represent a hydrogen atom, a C$_1$–C$_7$-alkyl group, a C$_3$–Cl$_{12}$-cycloalkyl group, a trifluoromethyl group, a C$_1$–C$_7$-alkoxy group or R$_1$ and R$_2$ together form an alkylene chain —(CH$_2$)$_r$—, where r is chosen from 2, 3 and 4;

p is chosen from 0, 1, 2, 3, 4 and 5;

Z represents a bond or a C$_2$–C$_7$-alkenylene radical;

R$_3$ represents a halogen atom; a C$_1$–C$_7$-alkyl group optionally substituted with one or more identical or different Y radicals; a C$_6$–C$_{10}$-aryl group optionally substituted with one or more identical or different Y radicals; a C$_6$–C$_{10}$-aryloxy group optionally substituted with one or more identical or different Y radicals; a C$_3$–C$_{12}$-cycloalkyl group optionally substituted with one or more identical or different Y radicals;

Y represents a halogen atom, C$_1$–C$_7$-alkyl, C$_1$–C$_7$-alkoxy, trifluoromethyl, carboxy, carbamoyl, (C$_1$–C$_7$) alkylcarbamoyl, di-(C$_1$–C$_7$)alkylcarbamoyl, C$_1$–C$_7$-alkoxycarbonyl, amino, C$_1$–C$_7$-alkylamino, di-(C$_1$–C$_7$)-alkylamino, nitro, cyano, hydroxy, trifluoromethoxy, C$_3$–C$_{12}$-cycloalkyl, sulfo, C$_1$–C$_7$-alkylthio, C$_1$–C$_7$-alkylsulfinyl, C$_1$–C$_7$-alkylsulfonyl, C$_2$–C$_8$-alkylcarbonyl, C$_2$–C$_8$-alkylthiocarbonyl, C$_2$–C$_8$-alkylcarbonylamino, or C$_6$–C$_{10}$-aryl;

E represents a divalent radical chosen from:

(i) —CO—NR$_4$— in which the carbonyl group is linked to —(CR$_1$R$_2$)$_p$— and R$_4$ represents the radical —(CH$_2$)$_q$—R$_5$ where q is chosen from 0 and 1; and where R$_5$ represents a hydrogen atom; a C$_1$–C$_7$-alkyl group, or a C$_6$–C$_{10}$-aryl group; or R$_5$ and R$_3$ together form a bond; and (ii) —NR$_4$— in which R$_4$ is as defined above;

n represents 0 or 1;

on the condition that —A(X)—(E)$_n$—(CR$_1$R$_2$)$_p$—Z—R$_3$ does not represent halophenyl, methylphenyl, dichlorophenyl, dimethylphenyl, 4-ethoxy-2-methylaminophenyl, 2-hydroxyphenyl substituted with a group X, 2-methoxyphenyl substituted with a group X and optionally substituted 2-fluorophenyl as defined above, and addition salts thereof with pharmaceutically acceptable bases.

2. Compound according to claim 1, in which A represents phenyl and n and p represent 0 and Z represents a bond.

3. Compound according to claim 1, in which A represents phenyl, n is equal to 1 and E represents —CO—NR$_4$—.

4. Compound according to claim 1, in which A represents phenyl, n and p are equal to 1, E represents —CO—NR$_4$—, R$_1$ and R$_2$ represent a hydrogen atom and Z represents a bond.

5. Compound according to claim 1, in which A represents naphthyl.

6. Compound according to claim 1 chosen from:

N-[3-chloro-4-(nitromethylcarbonylphenyl)]-2-methylphenylacetamide,

N-[3-chloro-4-(nitromethylcarbonylphenyl)]-2-trifluoromethylphenylacetamide,

N-[3-chloro-4-(nitromethylcarbonylphenyl)]-phenylacetamide,

N-[3-chloro-4-(nitromethylcarbonylphenyl)]-2-chlorophenylacetamide,

N-[3-chloro-4-(nitromethylcarbonylphenyl)]-4-chlorobenzamide, nitromethyl 2-trifluoromethoxyphenyl ketone, nitromethyl 2-methyl-1-naphthyl ketone, nitromethyl 3-chloro-2-naphthyl ketone, nitromethyl 6-methoxy-5-trifluoromethyl-1-naphthyl ketone.

7. A pharmaceutical composition comprising a pharmaceutically effective amount of at least one compound of formula (I) according to claim 1, in combination with at least one pharmaceutically acceptable vehicle.

8. Composition according to claim 7, in the form of an immediate-release tablet, a controlled-release tablet, a gelatin capsule, an injectable solution, a cream or a collyrium.

9. A composition according to claim 7 wherein the pharmaceutically acceptable amount of a compound of formula (I) is an aldose reductase inhibiting amount.

10. A process for the preparation of a compound of formula (I) according to claim 1, comprising treating an acid of formula

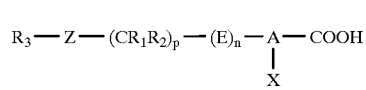

(II)

in which R$_1$, R$_2$, R$_3$, Z, E, n, p, A and X are as defined in claim 1, with a mixture of nitromethane and di(C$_1$–C$_7$)alkyl cyanophosphonate in the presence of a base.

* * * * *